United States Patent [19]

Kimura et al.

[11] Patent Number: 4,535,073

[45] Date of Patent: Aug. 13, 1985

[54] ANTIHYPERTENSIVE PHOSPHONO DERIVATIVES OF HANTZSCH DIHYDROPYRIDINES

[75] Inventors: Kiyoshi Kimura, Takatsuki; Iwao Morita, Tsuzuki; Seiichiro Morimura, Moriyama, all of Japan

[73] Assignee: Nippon Shinyaku Co Limited, Japan

[21] Appl. No.: 585,574

[22] Filed: Mar. 2, 1984

[30] Foreign Application Priority Data

Mar. 4, 1983 [JP]  Japan .................................. 58-36211

[51] Int. Cl.³ .................. A61K 31/675; C07D 211/92; C07D 401/12
[52] U.S. Cl. ...................................... 514/89; 546/21; 544/337; 260/239.6
[58] Field of Search ......................... 546/21; 544/337; 424/266, 200; 260/239.6

[56] References Cited

PUBLICATIONS

Issleib, et al., "Contributions to the Reaction Behavior of Oxoalkanephosphonic Acid Dialkyl Esters", J. Prakt. Chem. vol. 318(2), pp. 207–220 (1976).
Hackh's Chemical Dictionary, Fourth Edition, p. 62.

*Primary Examiner*—Henry R. Jiles
*Assistant Examiner*—Dale A. Bjorkman
*Attorney, Agent, or Firm*—Jacobs & Jacobs

[57] ABSTRACT

Dihydropyridine derivatives of Formula (I) and pharmaceutically acceptable salts thereof

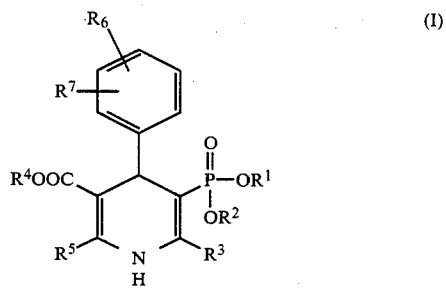

in which $R^1$–$R^7$ are as defined, methods of preparing these compounds and pharmaceutical compositions and methods of using these compounds for the treatment of heart disease, circulatory disorders and hypertension.

33 Claims, No Drawings

ANTIHYPERTENSIVE PHOSPHONO DERIVATIVES OF HANTZSCH DIHYDROPYRIDINES

The present invention is directed to 1,4-Dihydropyridine-3-carboxylates represented by the formula (I) and pharmaceutically acceptable salts thereof:

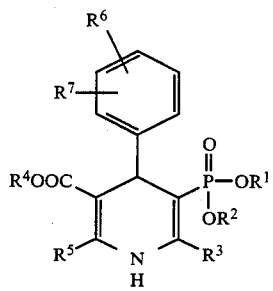

in which:

$R^1$ and $R^2$ are same or different and are hydrogen; alkyl of 1 to 10 carbon atoms, alkenyl of 2 to 10 carbon atoms, alkynyl of 2 to 10 carbon atoms, cycloalkyl of 3 to 7 carbon atoms, aryl of 6 to 10 carbon atoms, arylalkyl of 7 to 9 carbon atoms, or cycloalkyl-lower alkyl of 3 to 7 carbon atoms in the cycloalkyl moiety, unsubstituted or substituted by halogen or alkoxy of 1 to 4 carbon atoms; or tetrahydrofurfuryl unsubstituted or substituted by alkyl of 1 to 3 carbon atoms;

$R_3$ is lower alkyl, $R_4$ is hydrogen; alkyl of 1 to 10 carbon atoms, alkenyl of 2 to 10 carbon atoms, alkynyl of 2 to 10 carbon atoms, cycloalkyl of 3 to 7 carbon atoms, cycloalkenyl of 3 to 7 carbon atoms, aryl of 6 to 10 carbon atoms, or cycloalkyl-lower alkyl or cycloalkenyl-lower alkyl of 3 to 7 carbon atoms in the cyclic moiety, unsubstituted or substituted by alkoxy of 1 to 3 carbon atoms, aryloxy of 6 to 10 carbon atoms in the aryloxy moiety, aralkyloxy of 6 to 10 carbon atoms in the aralkyloxy moiety, amino, mono- or di-lower alkylamino, alkylthio of 1 to 3 carbon atoms, mono- or di-lower alkylamino-lower alkyl, alkylthioalkyl of 1 to 3 carbon atoms in both alkyl moieties, pyridyl or pyridyl-lower alkyl; tetrahydrofurfuryl unsubstituted or substituted by alkyl of 1 to 3 carbon atoms;

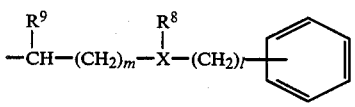

in which X is N or O, $R^8$ is lower alkyl or lower alkenyl when X is N and is not present when X is O, $R^9$ is hydrogen, alkyl of 1 to 3 carbon atoms, phenyl, or

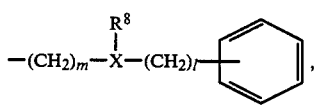

l is an integer of 0 to 2, and m is an integer of 1 to 4; or

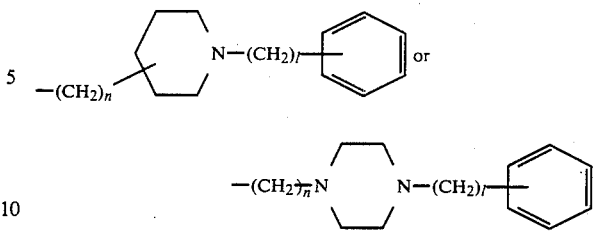

in which l is as defined above and n is an integer of 0 to 2;

$R^5$ is lower alkyl; and $R^6$ and $R^7$ are same or different and are hydrogen, nitro, cyano, trifluoromethyl, halogen, azide, alkoxycarbonyl of 1 to 3 carbon atoms in the alkoxy moiety, aminocarbonyl, sulfamyl, alkylsulfonyl of 1 to 3 carbon atoms in the alkyl moiety or difluoromethoxy.

The present invention also provides pharmaceutical compositions comprising compounds (I) and methods of using compounds (I) for treatment of disorders in animals, as will be described in detail below.

As used herein, the term "lower" means a group containing 1 to 6, preferably 1 to 3, carbon atoms.

Suitably, $R^1$, $R^2$ or $R^4$ may be straight or branched chain alkyl of 1 to 10 carbon atoms, such as methyl, ethyl, n-propyl, isopropyl, n-butyl, isobutyl, secondary butyl, tertiary butyl, n-pentyl, isopentyl, secondary pentyl, neopentyl, tertiary pentyl, 1,2-dimethylpropyl, n-hexyl, isohexyl, 3,3-dimethyl-1-butyl, 3,3-dimethyl-2-butyl, 1-methylpentyl, 1-ethylbutyl, n-heptyl, 1-methylhexyl, 1-ethylpentyl, n-octyl and the like, but preferably the alkyl will be lower alkyl.

$R^1$, $R^2$ or $R^4$ may also be alkenyl or alkynyl of 2 to 10, preferably 3 to 5, carbon atoms, such as allyl, crotyl, beta-methallyl, 1-methyl-2-butenyl, prenyl and the like.

$R^1$, $R^2$ or $R^4$ may also be cycloalkyl, and $R^4$ may be cycloalkenyl, of 3 to 7 carbon atoms, preferably 3 to 5 carbon atoms, and comprised of one or more rings, such as cyclopropyl, cyclobutyl, cyclopentyl, cyclopropenyl, cyclobutenyl, cyclopentenyl and the like.

$R^1$, $R^2$ or $R^4$ may also be aryl of 6 to 10 carbon atoms, with one or more rings, preferably phenyl.

$R^1$, $R^2$, or $R^4$ may also be cycloalkylalkyl, or arylalkyl, and $R^4$ may be cycloalkenyl or arylalkenyl, wherein the cycloalkyl, cycloalkenyl, and aryl moieties are defined above and the alkyl and alkenyl moieties contain up to 6, preferably up to 3 carbon atoms, such as cyclopropylmethyl, cyclobutylmethyl, cyclopentylmethyl, cyclopropylallyl, benzyl, phenethyl, cinnamyl and the like.

$R^1$, $R^2$ and $R^4$ may also be said alkyl, alkenyl or alkynyl as defined above substituted by alkoxy of 1 to 3 carbon atoms, preferably lower alkoxy, such as beta-methoxyethyl, beta-ethoxyethyl, beta-n-propoxyethyl, beta-isopropoxyethyl, 3-methyl-3-methoxy-butyl, 1,3-dimethoxy-2-propyl and the like.

Suitable lower alkyl groups for $R^3$ and $R^5$ are those of 1 to 6 carbon atoms, such as set forth above, such as methyl, ethyl, propyl and the like.

$R^4$ may be, in addition to that set forth above, aralkyloxyalkyl and aryloxyalkyl, wherein the alkyl moiety is lower alkyl, the aralkyloxy moiety is preferably phenyl-lower alkoxy and the aryloxy moiety is preferably phenoxy, such as beta-benzyloxyethyl, beta-phenethyloxyethyl, beta-phenoxyethyl and the like. Further suitable examples of R⁴ include methylthio, 2-methylthioethyl, methylamino, 2-dimethylaminoethyl, 3-dimethylaminopropyl, 2-pyridylmethyl, 3-pyridylmethyl, 2-pyridylethyl, 2-(3-pyridyl)ethyl, 4-pyridylmethyl, 2-(4-pyridyl)ethyl and the like.

Examples of the group represented by the formula

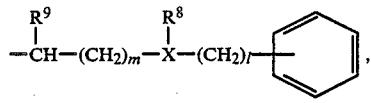

include 2-(N benzyl-N-methylamino)-ethyl, 2-(N-phenethyl-N-methylamino)-ethyl, 3-(N-benzyl-N-methylamino)-propyl, 4-(N-benzyl-N-methylamino)-butyl, 5-(N-benzyl-N-methylamino)-pentyl, 2-(N-benzyl-N-methylamino)-1-phenyl-ethyl, 2-(N-benzyl-N-methylamino)-1-phenylethyl, 2-(N-benzyl-N-methylamino)-1-(N-benzyl-N-methylaminomethyl)ethyl and the like.

Examples of the groups represented by the formula

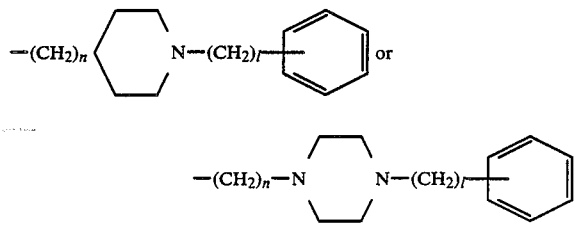

include N-benzyl-4-piperidinyl, N-benzyl-3-piperidinyl, N-benzyl-2-piperidinyl, N-phenyl-4-piperidinyl, N-phenethyl-4-piperidinyl, 2-(4-benzyl-1-piperazinyl)ethyl, 2-(4-phenethyl-1-piperazinyl)ethyl, 3-(4-benzyl-1-piperazinyl)propyl and the like.

Examples of the compounds covered by the present invention are, in addition to the compounds listed in examples later in this specification, as follows: methyl 2,6-dimethyl-4-(3-nitrophenyl)-5-di-sec-pentyloxyphosphinyl-1,4-dihydropyridine-3-carboxylate; methyl 2,6-dimethyl-5-di-(1,2-dimethylpropoxy)-phosphinyl-4-(3-nitrophenyl)-1,4-dihydropyridine-3-carboxylate; methyl 2,6-dimethyl-4-(3-nitrophenyl)-5-di-n-propoxyphosphinyl-1,4-dihydropyridinecarboxylate; methyl 2,6-dimethyl-5-di-(1-methylpentyloxy)-phosphinyl-4-(3-nitrophenyl)-1,4-dihydropyridine-3-carboxylate; methyl 5-di-(1-ethylbutoxy)-phosphinyl-2,6-dimethyl-4-(3-nitrophenyl)-1,4-dihydropyridine-3-carboxylate; methyl 2,6-dimethyl-4-(3-nitrophenyl)-5-di-(2-isopropoxyethoxy)-phosphinyl-1,4-dihydropyridine-3-carboxylate; methyl 5-dicrotyloxyphosphinyl-2,6-dimethyl-4-(3-nitrophenyl)-1,4-dihydropyridine-3-carboxylate; methyl 5-dimethallyloxyphosphinyl-2,6-dimethyl-4-(3-nitrophenyl)-1,4-dihydropyridine-3-carboxylate; methyl 2,6-dimethyl-5-di-(1-methyl-2-propenyloxy)-phosphinyl-4-(3-nitrophenyl)-1,4-dihydropyridine-3-carboxylate; methyl 2,6-dimethyl-4-(3-nitrophenyl)-5-diprenyloxyphosphinyl-1,4-dihydropyridine-3-carboxylate; methyl 5-dicyclopropylmethyloxyphosphinyl-2,6-dimethyl-4-(3-nitrophenyl)-1,4-dihydropyridine-3-carboxylate; methyl 2,6-dimethyl-4-(3-nitrophenyl)-5-di-(tetrahydrofurfuryloxy)-phosphinyl-1,4-dihydropyridine-3-carboxylate; methyl 5-difurfuryloxyphosphinyl-2,6-dimethyl-4-(3-nitrophenyl)-1,4-dihydropyridine-3-carboxylate; 2-dimethylaminoethyl 5-dimethoxyphosphinyl-2,6-dimethyl-4-(3-nitrophenyl)-1,4-dihydropyridine-3-carboxylate; 2-propoxyethyl 5-dimethoxyphosphinyl-2,6-dimethyl-4-(3-nitrophenyl)-1,4-dihydropyridine-3-carboxylate; 2-dimethylaminoethyl 5-diethoxyphosphinyl-2,6-dimethyl-4-(3-nitrophenyl)-1,4-dihydropyridine-3-carboxylate; 2-n-propoxyethyl 5-diethoxyphosphinyl-2,6-dimethyl-4-(3-nitrophenyl)-1,4-dihydropyridine-3-cabroxylate; 2-(N-benzyl-N-methylamino)-ethyl 2,6-dimethyl-4-(3-nitrophenyl)-5-di-sec-pentyloxyphosphinyl-1,4-dihydropyridine-3-carboxylate; 2-(N-benzyl-N-methylamino)-ethyl 2,6-dimethyl-5-di-(1,2-dimethylpropoxy)-phosphinyl-4-(3-nitrophenyl)-1,4-dihydropyridine-3-carboxylate; 2-(N-benzyl-N-metylamino)-ethyl 2,6-dimethyl-4-(3-nitrophenyl)-5-di-n-pentyloxyphosphinyl-1,4-dihydropyridine-3-carboxylate; 2-(N-benzyl-N-methylamino)-ethyl 2,6-dimethyl-5-di-(1-methylpentyloxy)-phosphinyl-4-(3-nitrophenyl)-1,4-dihydropyridine-3-carboxylate; 2-(N-benzyl-N-methylamino)-ethyl 5-di-(1-ethylbutoxy)-phosphinyl-2,6-dimethyl-4-(3-nitrophenyl)-1,4-dihydropyridine-3-carboxylate; ethyl 5-di-(2-methoxyethoxy)-phosphinyl-2,6-dimethyl-4-(3-nitrophenyl)-1,4-dihydropyridine-3-carboxylate; isopropyl 5-di-(2-methoxyethoxy)-phosphinyl-2,6-dimethyl-4-(3-nitrophenyl)-1,4-dihdyropyridne-3-carboxylate; 2-dimethylaminoethyl 5-di-(2-methoxyethoxy)-phosphinyl-2,6-dimethyl-4-(3-nitrophenyl)-1,4-dihydropyridine-3-carboxylate; 2-n-propoxyethyl 5-di-(2-methoxyethoxy)-phosphinyl-2,6-dimethyl-4-(3-nitrophenyl)-1,4-dihydropyridine-3-carboxylate; N-benzyl-4-piperidinyl 5-di-(2-methoxyethoxy)-phosphinyl-2,6-dimethyl-4-(3-nitrophenyl)-1,4-dihydropyridine-3-carboxylate; 2-n-propoxyethyl 5-di-(2-ethoxyethoxy)-phosphinyl-2,6-dimethyl-4-(3-nitrophenyl)-1,4-dihydropyridine-3-carboxylate; 2-(N-benzyl-N-methylamino)-ethyl 2,6-dimethyl-4-(3-nitrophenyl)-5-di-(2-isopropoxyethoxy)-phosphinyl-1,4-dihydropyridine-3-carboxylate; 2-dimethylaminoethyl 5-diallyloxyphosphinyl-2,6-dimethyl-4-(3-nitrophenyl)-1,4-dihydropyridine-3-carboxylate; 2-n-propoxyethyl 5-diallyloxyphosphinyl-2,6-dimethyl-4-(3-nitrophenyl)-1,4-dihydropyridine-3-carboxylate; 2-(N-benzyl-N-methylamino)-ethyl 5-dicrotyloxyphosphinyl-2,6-dimethyl-4-(3-nitrophenyl)-1,4-dihydropyridine-3-carboxylate; 2-(N-benzyl-N-methylamino)-ethyl 5-dimetallyloxyphosphinyl-2,6-dimethyl-4-(3-nitrophenyl)-1,4-dihydropyridine-3-carboxylate; 2-(N-benzyl-N-methylamino)-ethyl 5-dicyclopropylmethyloxyphosphinyl-2,6-dimethyl-4-(3-nitrophenyl)-1,4-dihydropyridine-3-carboxylate; 2-(N-benzyl-N-methylamino)-ethyl 2,6-dimethyl-4-(3-nitrophenyl)-5-di-(tetrahydrofurfuryloxy)-phosphinyl-1,4-dihydropyridine-3-carboxylate; methyl 5-dimethoxyphosphinyl-2,6-dimethyl-4-(2-nitrophenyl)-1,4-dihydropyridine-3-carboxylate; 2-(N-benzyl-N-methylamino)-ethyl 5-dimethoxyphosphinyl-2,6-dimethyl-4-(2-nitrophenyl)-1,4-dihydropyridine-3-carboxylate; methyl 5-di-(2-methoxyethoxy)-phosphinyl-2,6-dimethyl-4-(2-nitrophenyl)-1,4-dihydropyridine-3-carboxylate; 2-(N-benzyl-N-methylamino)-ethyl 5-di-(2-methoxyethoxy)-phosphinyl-2,6-dimethyl-4-(2-nitrophenyl)-1,4-dihydropyridine-3-carboxylate; methyl 5-diallyloxyphosphinyl-2,6-dimethyl-4-(2-nitrophenyl)-1,4-dihydropyridine-3-carboxylate; 2-(N-benzyl-N-methylamino)-ethyl-5-diallyloxyphosphinyl-2,6-dimethyl-4-(2-nitrophenyl)-1,4-dihydropyridine-3-carboxylate; methyl 5-di-(2-methoxyethoxy-phosphinyl-2,6-dimethyl-4-(2-trifluoromethylphenyl)-1,4-dihydropyridine-3-carboxylate; 2-(N-benzyl-N-methylamino)-ethyl 5-di-(2-methoxyethoxy)-phosphinyl-2,6-dimethyl-4-(2-trifluoromethylphenyl)-1,4-dihydropyridine-3-carboxylate; methyl 5-diallyloxyphosphinyl-2,6-dimethyl-4-(2-trifluoromethylphenyl)-1,4-dihydropyridine-3-carboxylate; 2-(N-benzyl-N-methylamino)-ethyl 5-diallyloxyphosphinyl-2,6-dimethyl-4-(2-trifluoromethyl)-phenyl)-1,4-dihydropyridine-3-carboxylate; methyl 5-di-(2-methoxyethoxy)-phosphinyl-2,6-dimethyl-4-(3-trifluoromethylphenyl)-1,4-dihydropyridine-3-carboxylate; 2-(N-benzyl-N-methylamino)-ethyl 5-di-(2-methoxyethoxy)-phosphinyl 2,6-dimethyl-4-(3-trifluoromethylphenyl)-1,4-dihydropyridine-3-carboxylate; methyl 5-diallyloxyphosphinyl-2,6-dimethyl-4-(3-trifluoromethylphenyl)-1,4-dihydropyridine-3-carboxylate; 2-(N-benzyl-N-methylamino)-ethyl 5-diallyloxyphosphinyl-2,6-dimethyl-4-(3-trifluoromethylphenyl)-1,4-dihydropyridine-3-carboxylate.

The compounds I have asymmetric carbon atom(s) and all the optically active compounds and mixtures thereof are within the scope of the present invention. Racemic compounds may, if desired, be separated by treating with an optically active acid when the present invention compound is a base and the optically active base can be obtained from the resulting salt. When the compound is an acid, the optically active acid can be similarly obtained by treatment with an optically active base.

The compound dimethyl 2,6-dimethyl-4-(2-nitrophenyl)-1,4-dihydropyridine-3,5-dicarboxylate (generic name: nifedipine) is known as a compound exhibiting vasodilating and hypotensive activity. The present invention now provides 1,4-dihydropyridine-3-carboxylate derivatives of the formula (I) and salts thereof, which show marked vasodilating and hypotensive activity with low toxicity.

The article by von K. Issleid, R. Wolff und M. Lengies; J. prakt. Chemie, 318, pages 207–220, 1976 reports the following compounds of formula (VII) below, but these compounds do not exhibit hypotensive activity:

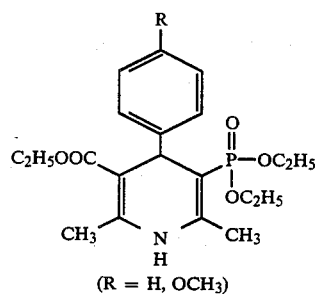

(R = H, OCH₃)

An object of the present invention is that, by introducing various electro-negative groups into the phenyl group substituted at the 4-position of 1,4-dihydropyridine, novel and excellent derivatives exhibiting marked vasodilating and anti-hypertensive activity are obtained.

Suitable manufacturing routes for the synthesis of the present invention compounds (I) are exemplified as follows.

Method 1.

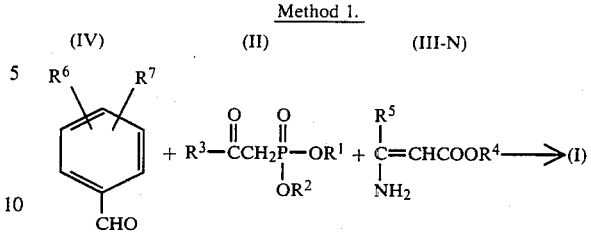

(in which meanings of $R^1$, $R^2$, $R^3$, $R^4$, $R^5$, $R^6$ and $R^7$ are the same as already defined)

(III-N) is the enaminoester of

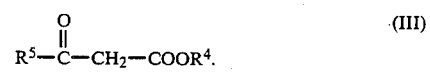

Thus, compounds (IV),(II) and (III-N) are mixed preferably in a molar ratio of 1:0.8:0.8 to 1:4:4 and, more preferably, in a molar ratio of 1:0.9:0.9 to 1:1.5:1.5. The reaction is conducted at room temperature to 150° C., more preferably 40° to 100° C., in the presence or absence of alcohols such as methanol, ethanol, isopropanol, etc., aromatic hydrocarbons such as benzene, toluene, etc., halogenated hydrocarbons such as chloroform, carbon tetrachloride, etc., ethers such as tetrahydrofuran, dioxane, etc., non-protonic solvents such as acetonitrile, dimethyl formamide, etc., or water.

Separation of desired compound from the reaction mixture is carried out by conventional methods such as, for example, concentration, extraction, column chromatography, recrystallization, and the like.

Other manufacture methods are exemplified hereinafter with reaction formulas. Those manufacture methods may be conducted by or with the same molar ratio, reaction solvent, reaction temperature, separation methods, etc.

Method 2.

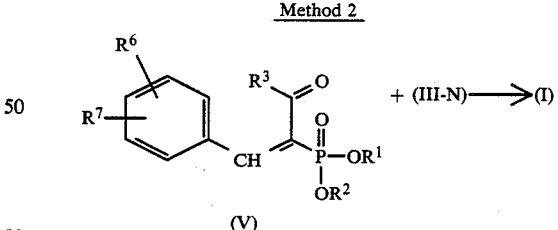

(in which meanings of $R^1$, $R^2$, $R^3$, $R^4$, $R^5$, $R^6$ and $R^7$ are the same as already defined)

The compound (V) used as a starting material can easily be obtained by a dehydrative condensation of (IV) and (II) used in the manufacture method 1 in an organic solvent.

Method 3.

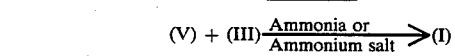

Method 4.

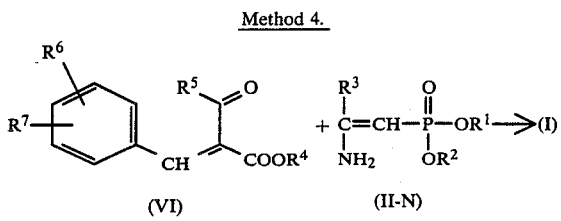

(in which meanings of $R^1$, $R^2$, $R^3$, $R^4$, $R^5$, $R^6$ and $R^7$ are the same as already defined)

Method 5.

Method 6.

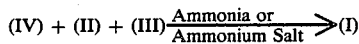

Ammonium salts hereinabove include ammonium acetate, ammonium carbonate, ammonium bicarbonate, and the like.

Phosphonic acid esters represented by formula (II) used as starting material are known in literatures or can be manufactured by methods known in literatures such as, for example, A. N. Pudovik and V. P. Aver'yanoura, Zhur. Obshch. Doklady Akad. Nauk S. S. S. R., 101, pages 889–892 (1955).

beta-Ketocarboxylic acid esters represented by formula (III) used as a starting material are known in literatures or can be manufactured by methods known in literatures such as, for example, D. Borrmann "Umsetzung von Diketen mit Alkoholen, Phenolen und Mercaptanen" in Houben-Weyl, Methoden der organischen Chemie, Vol. VII/4, page 230 (1968); Y. Oikawa, K. Sugano and O. Yonemitsu, J. Org. Chem., 43, page 2087 (1978).

Enaminoesters represented by formula (III-N) used as a starting material are known in literatures or can be manufactured by methods known in literatures such as, for example, A. C. Cope, et al., J. Am. Chem. Soc., 67, page 1017 (1945).

Enaminoesters of formula (II-N) can also be manufactured by the same methods as in (III-N).

Aromatic aldehydes (IV) used as starting material are known in literatures or can be manufactured by methods known in literatures such as, for example, E. Mosettig, Organic Reactions, VII, pages 218 et seq. (1954).

Benzylidene derivatives (V) used as starting material are manufactured by known methods in literatures such as, for example, A. N. Pudoruk, G. E. Yastrebova and V. I. Nikitina, Zh. Obshch. Khim. 37, pages 510–511 (1967) and R. Wolff und M. Lengies, J. prakt. Chem. 318, pages 207–220 (1976). Examples are given in References Examples disclosed later.

Benzylidene derivatives (VI) used as starting material are known in literatures or can be manufactured by known methods in literatures such as, for example, G. Jones, "The Knoevenagel Condensation" in Organic Reactios, Vol. XV, pages 204 et seq (1967).

Now, manufacture methods of starting materials for the present invention compounds (I) are illustrated in detail. However, the present invention is not limited thereto.

Reference Example 1.

To 300 ml of toluene were added 38.2 grams of dimethyl acetonylphosphonate and m-benzaldehyde, then 1.96 grams of piperidine and 2 ml of acetic acid were added thereto, and the mixture was heated to reflux for 16 hours with stirring. The reaction was conducted using a water remover so that water produced thereby was taken away. After cooled, the reaction solution was washed with 5% sodium hydroxide solution, then with 20% sodium bisulfite solution, and finally with water. Then it was dried, toluene was evaporated therefrom, and the residue was purified by subjecting to a silica gel column chromatography (350 grams of silica gel being used; eluting solution was a mixture of n-hexane and ethyl acetate) to afford 42.6 grams of dimethyl 1-(3-nitrobenzylidene)-acetonylphosphonate, pale brown oil, yield 65%. IR spectra (film, $cm^{-1}$): 1705, 1615, 1535, 1360, 1265, 1060, 1035, 820. NMR spectra ($CDCl_3$, δ): 2.30 (3H, s), 3.72 (6H, d, J=11 Hz), 7.3–7.8 (3H, m), 8.0–8.3 (2H, m).

The following compounds were also manufactured by the same way as in Reference Example 1.

Diethyl 1-(3-nitrobenzylidene)-acetonylphosphonate. Pale yellowish brown oil. Yield 65%. IR (film, $cm^{-1}$): 1705, 1615, 1535, 1355, 1260.

Di-isopropyl 1-(3-nitrobenzylidene)-acetonylphosphonate. Pale brown oil. Yield 60%. IR (film, $cm^{-1}$): 1705, 1615, 1535, 1355, 1260.

n-Propyl 1-(3-nitrobenzylidene)-acetonylphosphonate. Pale brown oil. Yield 71%. IR (film, $cm^{-1}$): 1705, 1615, 1535, 1355, 1260.

Di-n-butyl 1-(3-nitrobenzylidene)-acetonylphosphonate. Pale brown oil. Yield 62%. IR (film, $cm^{-1}$): 1710, 1615, 1535, 1360, 1255.

Di-isobutyl 1-(3-nitrobenzylidene)-acetonylphosphonate. Pale yellow crystals, melting point 81°–82° C. (ether). Yield 57%. IR (KBr, $cm^{-1}$): 1705, 1615, 1535, 1355, 1255.

Di-sec-butyl 1-(3-nitrobenzylidene)-acetonylphosphonate. Pale brown oil. Yield 58%. IR (film, $cm^{-1}$): 1710, 1620, 1535, 1360, 1255.

Diisopentyl 1-(3-nitrobenzylidene)-acetonylphosphonate. Pale brown oil. Yield 55%. IR (film, $cm^{-1}$): 1705, 1615, 1530, 1350, 1260.

Di-n-pentyl 1-(3-nitrobenzylidene)-acetonylphosphonate. Pale brown oil. Yield 48%. IR (film, $cm^{-1}$): 1710, 1615, 1530, 1350, 1260.

Di-sec-pentyl 1-(3-nitrobenzylidene)-acetonylphosphonate. Pale brown oil. Yield 56%. IR (film, $cm^{-1}$): 1710, 1610, 1530, 1350, 1255.

Dineopentyl 1-(3-nitrobenzylidene)-acetonylphosphonate. Pale yellow crystals, melting point 139°–140° C. (ether). Yield 50%. IR (KBr, $cm^{-1}$): 1710, 1610, 1530, 1350, 1250.

Dicyclopentyl 1-(3-nitrobenzylidene)-acetonylphosphonate. Pale brown oil. Yield 52%. IR (film, $cm^{-1}$): 1710, 1615, 1535, 1355, 1260.

Diphenyl 1-(3-nitrobenzylidene)-acetonylphosphonate. Pale yellow crystals, melting point 108°–111° C. (ether). Yield 45%. IR (film, $cm^{-1}$): 1710, 1615, 1535, 1355, 1255.

Di-2-methoxyethyl 1-(3-nitrobenzylidene)-acetonylphosphonate. Pale yellow oil. Yield 44%. IR (film, $cm^{-1}$): 1700, 1610, 1530, 1350, 1255.

Diallyl 1-(3-nitrobenzylidene)-acetonylphosphonate. Pale yellow oil, Yield 62%. IR (film, $cm^{-1}$): 1705, 1615, 1535, 1355, 1250, 1050, 1000.

Diisopropyl 1-(2-chlorobenzylidene)-acetonylphosphonate. Pale yellow oil. IR (film, cm$^{-1}$): 1705, 1615, 1260, 1055, 1000, 990.

Diisopropyl 1-(3-chlorobenzylidene)-acetonylphosphonate. Pale yellow oil. IR (film, cm$^{-1}$): 1700, 1610, 1570, 1255, 1050, 1000.

Diisopropyl 1-(2-cyanobenzylidene)-acetonylphosphonate. Pale yellow oil. IR (film, cm$^{-1}$): 2240, 1700, 1620, 1595, 1250, 1050, 1040, 1000, 990.

Diisopropyl 1-(2-trifluoromethylbenzylidene)-acetonylphosphonate. Pale yellow oil. IR (film, cm$^{-1}$): 1710, 1615, 1580, 1320, 1260, 1175, 1120, 1050, 1035, 980.

Diisopropyl 1-(3-trifluoromethylbenzylidene)-acetonylphosphonate. Pale yellow oil. IR (film, cm$^{-1}$): 1710, 1615, 1335, 1260, 1130, 1000.

The compounds (I) of the invention and pharmaceutically acceptable salts thereof exhibit strong vasodilating and hypotensive activity and have low toxicity. Hence, they are useful in the treatment of diseases of the circulatory system in animals, including humans, such as, for example, hypertension, heart disease, arrythmia, angina pectoris, myocardial infarction, cerebral blood vessel and peripheral blood vessel circulatory disorders, and the like. The compounds (I) and their pharmaceutically acceptable salts thereof are particularly useful for their coronary artery dilating activity and anti-hypertensive activity.

Representative compounds (I) of the present invention and pharmaceutically acceptable salts thereof were tested to determine their coronary artery dilating activity and anti-hypertensive activity, using a known compound, as a control. The results are given below.

1. TEST METHOD AND RESULTS

(A) CORONARY ARTERY DILATING ACTIVITY

In accordance with Langendorff's method, the effect of the test compound given by intercoronary administration to a constantly perfused isolated guinea pig heart preparation was examined. The vasodilating activity was evaluated for each compound from the decreasing rate of perfusion pressure at each dose ($10^{-7}$, $10^{-6}$, and $10^{-5}$ grams/heart). The results are given in Table 1.

TABLE 1

| Compound Tested (Example Number) | Vasodilating Activity (%) At A Dosage Of | | |
|---|---|---|---|
| | $10^{-7}$ gram/heart | $10^{-6}$ gram/heart | $10^{-5}$ gram heart |
| 1 | 7.2 | 16.0 | 26.9 |
| 2 | 5.0 | 18.7 | 41.9 |
| 3 | 12.8 | 27.9 | 36.0 |
| 4 | 21.7 | 32.0 | 35.6 |
| 5 | 23.3 | 36.2 | 40.4 |
| 6 | 8.4 | 18.1 | 31.5 |
| 7 | 17.0 | 20.6 | 28.3 |
| 9 | 12.0 | 25.2 | 40.0 |
| 11 | 16.5 | 27.5 | 30.4 |
| 15 | 7.2 | 20.4 | 38.0 |
| 16 | 8.1 | 13.0 | 24.3 |
| 18 | 8.0 | 12.5 | 26.5 |
| 19 | 23.1 | 26.2 | 38.6 |
| 20a | 10.8 | 21.3 | 33.1 |
| 20b | 9.0 | 18.1 | 22.1 |
| 22 | 14.0 | 19.0 | 29.0 |
| 27 | 20.5 | 27.0 | 32.5 |
| 28 | 16.6 | 25.3 | 43.8 |
| 34 | 31.3 | 26.5 | 38.3 |
| 39 | 16.5 | 25.5 | 29.2 |
| 41 | 3.7 | 18.8 | 33.2 |
| 44 | 9.4 | 16.2 | 28.3 |
| 45 | 10.2 | 27.5 | 31.5 |

TABLE 1-continued

| Compound Tested (Example Number) | Vasodilating Activity (%) At A Dosage Of | | |
|---|---|---|---|
| | $10^{-7}$ gram/heart | $10^{-6}$ gram/heart | $10^{-5}$ gram heart |
| 47 | 8.1 | 13.3 | 28.5 |
| 48 | 25.3 | 34.5 | 35.7 |
| 50 | 12.0 | 24.4 | 31.1 |
| 52 | 18.1 | 28.0 | 37.0 |
| 60 | 11.5 | 19.2 | 38.0 |
| 62 | 17.8 | 23.1 | 42.6 |
| 63 | 18.9 | 17.0 | 30.7 |
| 65 | 30.2 | 41.5 | 45.7 |
| 82 | 30.6 | 38.8 | 47.2 |
| 91 | 36.7 | 50.3 | 63.2 |
| 99 | 16.1 | 20.9 | 38.3 |
| 131 | 11.3 | 13.4 | 28.8 |
| 145 | 14.2 | 32.0 | 43.6 |
| 149 | 16.0 | 34.9 | 52.8 |
| 153 | 10.7 | 23.7 | 41.6 |
| 154 | 2.3 | 31.7 | 52.6 |
| 156 | 15.4 | 22.2 | 35.8 |
| 159 | 62.0 | 72.0 | 74.3 |
| 160 | 15.4 | 30.4 | 39.8 |
| 162 | 26.9 | 29.3 | 33.2 |
| 163 | 12.0 | 38.7 | 44.9 |
| 166 | 16.2 | 32.8 | 53.2 |
| 168 | 10.5 | 61.0 | 68.3 |
| 170 | 37.1 | 48.3 | 59.6 |
| 173 | 23.1 | 35.5 | 47.7 |
| 174 | 10.9 | 39.5 | 51.0 |
| 177 | 17.4 | 18.1 | 28.0 |
| 178 | 10.2 | 36.1 | 43.0 |
| 179 | 28.4 | 61.3 | 66.3 |
| Diltiazem | 10.2 | 28.3 | 35.7 |

(B) ANTI-HYPERTENSIVE ACTIVITY

Normal rats were used. Under unanesthetized condition, the blood pressure of the femoral artery was measured by a pressure transducer and the anti-hypertensive activity of the test compounds was evaluated as follows.

The test compounds were administered per os with various doses (i.e. 3, 10, and 30 mg/kg) and the blood pressure at each dose was measured over a period of time. The blood pressure decreasing rate was reported as the maximum rate (%) of decrease of mean artery blood pressure in each group. The results are given in Table 2.

At the same time, the same test was carried out with two compounds represented by formula (VII) (R=hydrogen and OCH$_3$) but neither showed hypotensive activity at a dose of 30 mg/kg.

TABLE 2

| Compounds Tested (Example Number) | Anti-Hypertensive Activity (%) At A Dosage Of | | |
|---|---|---|---|
| | 3 mg/kg | 10 mg/kg | 30 mg/kg |
| 2 | 10.9 | 16.6 | 31.7 |
| 5 | 23.5 | 30.1 | 49.2 |
| 11 | 12.2 | 17.6 | 36.1 |
| 15 | 6.5 | 11.0 | 22.4 |
| 19 | 13.0 | 22.8 | 43.0 |
| 20a | 7.2 | 8.3 | 20.0 |
| 22 | 8.1 | 26.0 | 38.6 |
| 27 | 12.5 | 36.7 | 49.0 |
| 34 | 21.2 | 33.7 | 50.4 |
| 44 | 12.7 | 18.8 | 37.9 |
| 46 | 18.3 | 24.2 | 39.8 |
| 48 | 24.1 | 47.6 | 48.3 |
| 50 | 18.0 | 27.1 | 50.0 |
| 60 | 20.6 | 28.5 | 50.1 |
| 62 | 18.3 | 32.0 | 45.6 |
| 63 | 12.1 | 14.2 | 33.3 |
| 65 | 13.2 | 20.9 | 47.8 |
| 79 | 13.2 | 44.5 | 33.2 |

TABLE 2-continued

| Compounds Tested (Example Number) | Anti-Hypertensive Activity (%) At A Dosage Of | | |
|---|---|---|---|
| | 3 mg/kg | 10 mg/kg | 30 mg/kg |
| 82 | 37.2 | 38.1 | 46.0 |
| 86 | 11.9 | 27.4 | 34.1 |
| 89 | 5.3 | 28.2 | 49.6 |
| 90 | 20.2 | 26.4 | 36.8 |
| 91 | 15.1 | 43.3 | 38.7 |
| 94 | 8.5 | 23.1 | 38.7 |
| 99 | 28.5 | 44.4 | 45.7 |
| 100 | 3.8 | 16.5 | 33.6 |
| 131 | 17.2 | 25.5 | 42.3 |
| 145 | 12.6 | 24.5 | 48.9 |
| 151 | 16.8 | 27.5 | 43.3 |
| 162 | 2.8 | 34.9 | 51.9 |
| 164 | 21.3 | 37.7 | 39.7 |
| 166 | 3.1 | 34.4 | 44.5 |
| 170 | 10.3 | 29.7 | 34.2 |
| 179 | 12.9 | 37.4 | 47.8 |
| Diltiazem | — | 25.0 | 33.2 |

(C) ACUTE TOXICITY

Compounds (I) of the present invention show little toxicity and their $LD_{50}$ values by oral administration to rats are above 400 mg/kg.

The present invention thus provides a method for the treatment of heart disease, angina pectoris, hypertension, cardiac arrythmia, myocardial infarction, cerebral blood vessel disorders and peripheral blood vessel disorders in animals, including humans, by administering to the sufferer an effective amount of a compound of formula (I) or a pharmaceutically acceptable salt thereof.

The present invention also provides a pharmaceutical composition comprising an effective amount of the compound of formula (I) or a pharmaceutically acceptable salt thereof as the active agent in combination with a pharmaceutically acceptable, inert carrier or diluent therefor. Generally, the composition will comprise 0.1% to 99.5% preferably 0.5% to 90% of compound (I) or a pharmaceutically acceptable salt thereof.

The method of treatment of the present invention may be carried out by administering the compound (I) or pharmaceutically acceptable salt thereof as such, such as in the form of a powder, but more usually the compound (I) or pharmaceutically acceptable salt thereof will be administered in combination with a pharmaceutically acceptable, non-toxic, inert diluent or carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage unit can contain one, two, three, four or more single doses, or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 0.02 to 20 mg of the compound of the present invention, preferably 0.2 to 4 mg, per kg of body weight per day. In some instances, a sufficient therapeutic effect can be obtained at a lower dose, while in others a larger dose will be required. Most preferably, the daily dosage will be from 0.4 to 2 mg/kg of body weight.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such a an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, carboxymethylcellulose, calcium carboxymethylcellulose, calcium carbonate or sodium carbonate can also be added to improve the availability of the medicament when the capsule is ingested.

The powder described above may be dissolved and/or dispersed in vegetable oils, polyethylene glycol, glycerol, surface active agent or the like, and then packed in gelatin sheaths to prepare soft capsules.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free-flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of non-toxic alcoholic vehicles. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration. Non-toxic salts and salt solutions can be added to render the injection solution isotonic. Stabilizers, preservatives and emulsifiers can also be added.

Rectal administration can be effected utilizing suppositories, in which the compound is admixed with low-melting, water-soluble or insoluble solids such as polyethylene glycol, cocoa butter, higher esters as for example myristyl palmitate, or mixtures thereof.

To the pharmaceutical preparations of the present invention, there may also be added other pharmaceuticals, such as nitrites, beta-blockers, diuretic hypotensive drugs, and the like. These drugs may also be simultaneously given to patients together with the compounds (I) of the present invention.

While the routes of administration of the compound of the invention include oral, parenteral (i.e., intramuscular, intraperitoneal and intravenous), and rectal, oral administration is preferred.

The preferred pharmaceutical compositions are therefore those in a form suitable for oral administration, such as the solutions and suspensions described above.

The present invention is illustrated by the following non-limiting Examples.

EXAMPLE 1

To a mixture of 1.85 grams of dimethyl 1-(3-nitrobenzylidene)-acetonylphosphonate and 0.75 gram of methyl 3-aminocrotonate was added 25 ml of isopropanol and the mixture was heated to reflux for four hours with stirring. The reaction mixture was concentrated in vacuo, to the residue was added ether, the resulting crystals were collected by filtration, and recrystallized from ethyl acetate to afford 1.08 grams (yield 42%) of methyl 5-dimethoxyphosphinyl-2,6-dimethyl-4-(3-nitrophenyl)-1,4-dihydropyridine-3-carboxylate, pale yellow crystals, melting point 221°–3° C.

IR spectra (KBr, cm$^{-1}$): 3300, 3240, 1708, 1650, 1535, 1355.

NMR spectra (CDCl$_3$, δ): 2.31 (3H, d, J=2.5 Hz); 2.36 (3H, s); 3.35 (3H, d, J=11 Hz); 3.54 (3H, d, J=10 Hz); 3.65 (3H, s); 4.80 (1H, d, J=10 Hz); 6.01 (1H, d, J=5 Hz); 7.37 (1H, t, J=8 Hz); 7.61–7.68 (1H, m) 7.96–8.04 (1H, m) 8.11 (1H, t, J=2 Hz).

Elementary analysis for: $C_{17}H_{21}N_2O_7P$; Calculated (%): C: 51.52; H: 5.34; N: 7.07; Determined (%): C: 51.48; H: 5.57; N: 6.98.

EXAMPLE 2

To a mixture of 3.42 grams of dimethyl 1-(3-nitrobenzylidene)-acetonylphosphonate and 3.13 grams of 2-(N-benzyl-N-methylamino)-ethyl 3-aminocrotonate was added 50 ml of isopropanol and the mixture was heated to reflux for four hours with stirring. The reaction mixture was concentrated in vacuo, the residue was dissolved in ethyl acetate, to this was added 5% hydrochloric acid solution followed by separation, chloroform was added the lower layer followed by separation, the chloroform layer was washed with 5% calcium carbonate solution and then with water, and dried. Chloroform was evaporated in vacuo, the residue was purified by subjecting to silica gel column chromatography (100 grams of silica gel being used; eluting solution is ethyl acetate), and the resulting crystals were recrystallized from a mixture of ethyl acetate and ether to give 1.28 grams (yield 20%) of 2-(N-benzyl-N-methylamino)-ethyl 5-dimethoxyphosphinyl-2,6-dimethyl-4-(3-nitrophenyl)-1,4-dihydropyridine-3-carboxylate, pale yellow crystals, melting point 101°–3° C.

IR spectra (KBr, cm$^{-1}$): 3380, 3250, 3100, 1705, 1650, 1535, 1350.

NMR spectra (CDCl$_3$, δ): 2.20 (3H, s); 2.60~2.68 (2H, m); 3.33 (3H, d, J=11 Hz); 3.50 (2H, d, J=2 Hz); 3.54 (3H, d, J=11 Hz) 4.13~4.21 (2H, m); 4.82 (1H, d, J=10 Hz); 6.10 (1H, d, J=5 Hz); 7.26 (5H, s); 7.33 (1H, t, J=8 Hz); 7.69 (1H, d, J=8 Hz); 7.95~8.01 (1H, m); 8.12 (1H, t, J=2 Hz).

Elementary analysis for $C_{26}H_{32}N_3O_7P$, Calculated (%) C: 58.97; H: 6.09; N: 7.94; Determined (%) C: 58.92; H: 6.40; N: 7.94.

EXAMPLE 3

A mixture of 5.1 grams of diisopropyl 1-(3-nitrobenzylidene)-acetonylphosphonate and 2.69 grams of 2-n-propoxyethyl 3-aminocrotonate was added to 20 ml of isopropanol and the mixture was heated to reflux for eight hours with stirring. The reaction mixture was evaporated in vacuo, to the residue was added ether to crystallize, the crystals were collected by filtration, and recrystallized from a mixture of ethyl acetate and ether to afford 5.38 grams of 2-n-propoxyethyl 2,6-dimethyl-4-(3-nitrophenyl)-5-diisopropoxyphosphinyl-1,4-dihydropyridine-3-carboxylate, pale yellow crystals, melting point 125°–6° C. Yield 72%.

IR spectra (KBr, cm$^{-1}$): 3290, 3230, 3110, 1695, 1645, 1535, 1350, 1240, 1210, 980.

NMR spectra (CDCl$_3$, δ): 0.90 (3H, t, J=7.5 Hz); 0.95 (3H,d=6.2 Hz) 1.13 (3H,d,J=5.0 Hz); 1.15 (3H,d,J=8.0 Hz); 1.26 (3H,d,J=6.2 Hz); 1.48~1.62 (2H,m); 2.31 (3H,d,J=2.5 Hz); 2.35 (3H,s); 3.34~3.42 (2H,m); 3.59 (2H,t,J=5 Hz); 4.15~4.22 (2H,m); 4.29~4.50 (2H,m); 4.91 (1H, d, J=11.2 Hz); 6.10 (1H,d,J=5 Hz); 7.35 (1H,t,J=7.8 Hz); 7.71 (1H,d,J=7.8 Hz); 7.96~8.02 (1H,m) 8.12 (1H,t,J=2 Hz).

Elementary analysis for $C_{25}H_{37}N_2O_8P$, Calculated (%) C: 57.25; H: 7.11; N: 5.34; Determined (%) C: 57.10; H: 7.21; N: 5.34.

EXAMPLE 4

A mixture of 2.44 grams of diisopropyl acetonylphosphonate, 1.15 grams of methyl 3-aminocrotonate, and 1.51 grams of m-nitrobenzaldehyde was dissolved in 10 ml of isopropanol, then 290 mg of piperidine acetate was added thereto, and the mixture was heated to reflux for sixteen hours with stirring. The reaction solution was concentrated in vacuo, to the residue was added ether, the resulting crystals were collected by filtration, washed with ether and then with water, dried, and recrystallized from ethyl acetate to afford 1.57 grams (yield 34%) of methyl 2,6-dimethyl-4-(3-nitrophenyl)-5-diisopropoxyphosphinyl-1,4-dihydropyridine-3-carboxylate, melting point 205°–7° C.

IR spectra (KBr, cm$^{-1}$): 3270, 3200, 3080, 1705, 1645, 1530, 1500, 1350, 1240, 975.

NMR spectra (CDCl$_3$, δ): 0.99 (3H, d, J=6.2 Hz); 1.11 (3H,d, J=6.2 Hz); 1.16 (3H,d,J=6.2 Hz); 1.25 (3H,d,J=6.2 Hz); 2.29 (3H,d,J=2.5 Hz); 2.36 (3H, s); 3.65 (3H,s); 4.20~4.40 (1H,m); 4.40~4.58 (1H,m); 4.90 (1H, d, J=10.3 Hz); 5.83 (1H,d,J=5 Hz); 7.36 (1H,t,J=7.8 Hz) 7.67 (1H, d, J=7.8 Hz); 7.97~8.03 (1H, m); 8.13 (1H, t, J=2 Hz).

Elementary analysis for C$_{21}$H$_{29}$N$_2$O$_7$P, Calculated (%): C: 55.75; H: 6.46; N: 6.19; Determined (%): C: 55.39; H: 6.68; N: 6.21.

EXAMPLE 5

A mixture of 2.22 grams of diisopropyl acetonylphosphonate and 1.51 grams of m-nitrobenzaldehyde was added to 10 ml of isopropanol, 300 mg of piperidine acetate was added thereto, and the mixture was heated to reflux for three hours with stirring. To this was added 2.48 grams of 2-(N-benzyl-N-methylamino)-ethyl 3-aminocrotonate and the mixture was heated to reflux for another five hours with stirring. The reaction mixture was concentrated, the residue was dissolved in ethyl acetate, the solution was washed with 1N aqueous solution of sodium hydroxide, aqueous solution of sodium bisulfite, and water, successively, then separated after addition of 1N hydrochloric acid solution, to the lower layer was added chloform followed by separation, the chloroform layer was washed with 5% aqueous solution of potassium carbonate and then with water, and dried. Chloroform was evaporated therefrom in vacuo, the residue was purified by subjecting to silica gel column chromatography (100 grams of silica gel used; eluting solution: ethyl acetate) and the resulting crystals were recrystallized from ethyl acetate to afford 3.04 grams of 2-(N-benzyl-N-methylamino)-ethyl 2,6-dimethyl-4-(3-nitrophenyl)-5-diisopropoxyphosphinyl-1,4-dihydropyridine-3-carboxylate, melting point 113°–15° C., melting point of the hydrochloride 119° C.

IR spectra (KBr, cm$^{-1}$): 3270, 3210, 3080, 1700, 1645, 1530, 1500, 1355, 1235, 1215, 975.

NMR spectra (CDCl$_3$, δ): 0.96 (3H, d, J=6.2 Hz); 1.24 (3H, d, J=6 Hz); 2.19 (3H,S); 2.30 (3H,d,J=2.5 Hz); 2.34 (3H,s); 2.64 (2H,t,J=6 Hz); 3.49 (2H,s); 4.14~4.24 (2H,m); 4.26~4.60 (2H,m); 4.91 (1H,d,J=10.1 Hz); 5.79 (1H,d,J=5 Hz); 7.20~7.35 (6H,m); 7.69 (1H,d,J=8 Hz); 7.95~8.00 (1H,m); 8.13 (1H,t, J=1 Hz).

Elementary analysis for C$_{30}$H$_{40}$N$_3$O$_7$P, Calculated (%) C: 61.53; H: 6.88; N: 7.18; Determined (%) C: 61.32; H: 7.06; N: 7.14.

Similarly as in Examples 1 to 5 were prepared compounds as given in the following Examples 6 to 62.

EXAMPLE 6

Ethyl 5-dimethoxyphosphinyl-2,6-dimethyl-4-(3-nitrophenyl)-1,4-dihydropyridine-3-carboxylate. Melting point 155°–7° C.

Elementary analysis for C$_8$H$_{23}$N$_2$O$_7$P, Calculated (%): C: 52.69; H: 5.65; N: 6.83; Determiend (%): C: 52.77; H: 5.85; N: 6.82.

EXAMPLE 7

Isopropyl 5-dimethoxyphosphinyl-2,6-dimethyl-4-(3-nitrophenyl)-1,4-dihydropyridine-3-carboxylate. Melting point 171°–2° C.

Elementary analysis for C$_{19}$H$_{25}$N$_2$O$_7$P, Calculated (%): C: 53.77; H: 5.94; N: 6.60; Determined (%): C: 53.73; H: 6.09; N: 6.49.

EXAMPLE 8

Methyl 5-diethoxyphosphinyl-2,6-dimethyl-4-(3-nitrophenyl)-1,4-dihydroxypyridine-3-carboxylate. Melting point 179°–81° C.

Elementary analysis for: C$_{19}$H$_{25}$N$_2$O$_7$P, Calculated (%): C: 53.77; H: 5.94; N: 6.60; Determined (%): C: 53.56; H: 6.04; N: 6.41.

EXAMPLE 9

Ethyl 5-diethoxyphosphinyl-2,6-dimethyl-4-(3-nitrophenyl)-1,4-dihydropyridine-3-carboxylate. Melting point 135°–7° C.

Elementary analysis for: C$_{20}$H$_{27}$N$_2$O$_7$P, Calculated (%): C: 54.79; H: 6.21; N: 6.39; Determined (%): C: 54.44; H: 6.45; N: 6.23.

EXAMPLE 10

Isopropyl 5-diethoxyphosphinyl-2,6-dimethyl-4-(3-nitrophenyl)-1,4-dihydropyridne-3-carboxylate. Melting point 151°–2° C.

Elementary analysis for: C$_{21}$H$_{29}$N$_2$O$_7$P, Calculated (%): C: 55.75; H: 6.46; N: 6.19; Determined (%): C: 55.44; H: 6.64; N: 6.04.

EXAMPLE 11

2-(N-Benzyl-N-methylamino)-ethyl 5-diethoxyphosphinyl-2,6-dimethyl-4-(3-nitrophenyl)-1,4-dihydropyridine-3-carboxylate.

Melting point 77°–9° C.

Elementary analysis for: C$_{28}$H$_{36}$N$_3$O$_7$P, Calculated (%): C: 60.32; H: 6.51; N: 7.54; Determined (%): C: 60.07; H: 6.65; N: 7.35.

EXAMPLE 12

Ethyl 2,6-dimethyl-4-(3-nitrophenyl)-5-diisopropoxyphosphinyl-1,4-dihydropyridine-3-carboxylate. Melting point 152°–4° C.

Elementary analysis for: C$_{22}$H$_{31}$N$_2$O$_7$P, Calculated (%): C: 56.65; H: 6.70; N: 6.01; Determined (%): C: 56.29; H: 6.89; N: 5.96.

EXAMPLE 13

Isopropyl 2,6-dimethyl-4-(3-nitrophenyl)-5-diisopropoxyphosphinyl-1,4-dihydropyridine-3-carboxylate. Melting point 134°–6° C.

Elementary analysis for: C$_{23}$H$_{33}$N$_2$O$_7$P, Calcualted (%): C: 57.49; H: 6.92; N: 5.83; Determined (%): C: 57.31; H: 7.09; N: 5.78.

EXAMPLE 14

2-Dimethylaminoethyl 2,6-dimethyl-4-(3-nitrophenyl)-5-diisopropoxyphosphinyl-1,4-dihydropyridine-3-carboxylate. Melting point 122°–3° C.

Elementary analysis for: $C_{24}H_{36}N_3O_7P$, Calculated (%): C: 56.57; H: 7.12; N: 8.25; Determined (%): C: 56.35; H: 7.13; N: 8.05.

EXAMPLE 15

2-Benzyloxyethyl 2,6-dimethyl-4-(3-nitrophenyl)-5-diisopropoxyphosphinyl-1,4-dihydropyridine-3-carboxylate. Melting point 94°–5° C.

Elementary analysis for: $C_{29}H_{37}N_2O_8P$, Calculated (%): C: 60.83; H: 6.51; N: 4.89; Determined (%): C: 60.57; H: 6.78; N: 4.98.

EXAMPLE 16

2-Phenoxyethyl 2,6-dimethyl-4-(3-nitrophenyl)-5-diisopropoxyphosphinyl-1,4-dihydropyridine-3-carboxyalte. Melting point 144°–5° C.

Elementary analysis for: $C_{28}H_{35}N_2O_8P$, Calculated (%): C: 60.21; H: 6.32; N: 5.02; Determiend (%): C: 60.17; H: 6.55; N: 5.08.

EXAMPLE 17

Allyl 2,6-dimethyl-4-(3-nitrophenyl)-5-diisopropoxyphosphinyl-1,4-dihydropyridine-3-carboxylate. Melting point 145°–6° C.

Elementary analysis for: $C_{23}H_{31}N_2O_7P$, Calculated (%): C: 57.74; H: 6.53; N: 5.85; Determined (%): C: 57.56; H: 6.64; N: 5.70.

EXAMPLE 18

Cyclopentyl 2,6-dimethyl-4-(3-nitrophenyl)-5-diisopropoxyphisphinyl-1,4-dihydropyridine-3-carboxylate. Melting point 153°–4° C.

Elementary analysis for: $C_{25}H_{35}N_2O_7P$, Calculated (%): C: 59.28; H: 6.96; N: 5.53; Determined (%): C: 59.05; H: 7.11; N: 5.36.

EXAMPLE 19

N-Benzyl-4-piperidinyl 2,6-dimethyl-4-(3-nitrophenyl)-5-diisopropoxyphosphinyl-1,4-dihydropyridine-3-carboxylate. Melting point 186°–7° C.

Elementary analysis for: $C_{32}H_{42}N_3O_7P$, Calculated (%): C: 62.83; H: 6.92; N: 6.87; Determined (%): C: 62.68; H: 7.16; N: 6.68.

EXAMPLE 20

2-(N-Benzyl-N-methylamino)-1-phenylethyl 2,6-dimethyl-4-(3-nitrophenyl)-5-diisopropoxyphosphinyl-1,4-dihydropyridine-3-carboxylate. (Isomers due to diastereomers were separated)

(a) Melting point 148°–9° C.

Elementary analysis for: $C_{36}H_{44}N_3O_7P$, Calculated (%): C: 65.34; H: 6.70; N: 6.35; Determined (%): C: 65.10; H: 6.69; N: 6.24.

(b) Another isomer, melting point 101°–3° C.

Elementary analysis for: $C_{36}H_{44}N_3O_7P$, Calculated (%): C: 65.34; H: 6.70; N: 6.35; Determined (%): C: 65.01; H: 6.82; N: 6.18.

EXAMPLE 21

Ethyl 2,6-dimethyl-4-(3-nitrophenyl)-5-di-n-propoxyphosphinyl-1,4-dihydropyridine-3-carboxylate. Melting point 125°–6° C.

Elementary analysis for: $C_{22}H_{32}N_2O_7P$ Calculated (%): C: 56.64; H: 6.70; N: 6.01; Determined (%): C: 56.47; H: 6.84; N: 6.02.

EXAMPLE 22

2-(N-Benzyl-N-methylamino)-ethyl 2,6-dimethyl-4-(3-nitrophenyl)-5-di-n-propoxyphosphinyl-1,4-dihydropyridine-3-carboxylate. Pale yellow oil. Picrate melts at 104°–5° C.

Elementary analysis for: $C_{30}H_{40}N_3O_7P \cdot C_6H_3N_3O_7$ Calculated (%): C: 53.07; H: 5.32; N: 10.31; Determined (%): C: 53.92; H: 5.35; N: 10.27.

EXAMPLE 23

2-n-Propoxyethyl 2,6-dimethyl-4-(3-nitrophenyl)-5-di-n-propoxyphosphinyl-1,4-dihydropyridine-3-carboxylate. Melting point 80°–1° C.

Elementary analysis for: $C_{25}H_{37}N_2O_8P$, Calculated (%): C: 57.25; H: 7.11; N: 5.34; Determined (%): C: 57.10; H: 7.19; N: 5.35.

EXAMPLE 24

Methyl 2,6-dimethyl-4-(3-nitrophenyl)-5-di-n-propoxyphosphinyl-1,4-dihydropyridine-3-carboxylate. Melting point 174°–5° C.

Elementary analysis for: $C_{21}H_{29}N_2O_7P$, Calculated (%): C: 55.75; H: 6.46; N: 6.19; Determined (%): C: 55.51; H: 6.64; N: 6.20.

EXAMPLE 25

Methyl 5-diisobutoxyphosphinyl-2,6-dimethyl-4-(3-nitrophenyl)-1,4-dihydropyridine-3-carboxylate. Melting point 177°–8° C.

Elementary analysis for: $C_{23}H_{33}N_2O_7P$, Calculated (%): C: 57.49; H: 6.92; N: 5.83; Determined (%): C: 57.31; H: 7.19; N: 5.90.

EXAMPLE 26

Ethyl 5-diisobutoxyphosphinyl-2,6-dimethyl-4-(3-nitrophenyl)-1,4-dihydropyridine-3-carboxylate. Melting point 148°–9° C.

Elementary analysis for: $C_{24}H_{35}N_2O_7P$, Calculated (%): C: 58.29; H: 7.13; N: 5.66; Determined (%): C: 57.93; H: 7.41; N: 5.67.

EXAMPLE 27

2-(N-Benzyl-N-methylamino)-ethyl 5-diisobutoxyphosphinyl-2,6-dimethyl-4-(3-nitrophenyl)-1,4-dihydropyridine-3-carboxylate. Pale yellow oil. Picrate melts at 104°–6° C.

Elementary analysis for: $C_{32}H_{44}N_3O_7P \cdot C_6H_3N_3O_7$, Calculated (%): C: 54.16; H: 5.62; N: 9.97; Determined (%): C: 53.88; H: 5.69; N: 9.89.

EXAMPLE 28

2-Dimethylaminoethyl 5-diisobutoxyphosphinyl-2,6-dimethyl-4-(3-nitrophenyl)-1,4-dihydropyridine-3-carboxylate. Melting point 148.5°–9.5° C.

Elementary analysis for: $C_{26}H_{40}N_3O_7P$, Calculated (%): C: 58.09; H: 7.50; N: 7.82; Determined (%): C: 58.34; H: 7.71; N: 7.96.

EXAMPLE 29

2-n-Propoxyethyl 5-diisobutoxyphosphinyl-2,6-dimethyl-4-(3-nitrophenyl)-1,4-dihydropyridine-3-carboxylate. Melting point 103°–4° C.

Elementary analysis for: $C_{27}H_{41}N_2O_8P$; Calculated (%): C: 58.69; H: 7.48; N: 5.07; Determined (%): C: 58.70; H: 7.60; N: 5.19.

EXAMPLE 30

N-Benzyl-4-piperidinyl 5-diisobutoxyphosphinyl-2,6-dimethyl-4-(3-nitrophenyl)-1,4-dihydropyridine-3-carboxylate. Melting point 153°–4° C.

Elementary analysis for: $C_{34}H_{46}N_3O_7P$, Calculated (%): C: 63.84; H: 7.25; N: 6.57; Determined (%): C: 63.66; H: 7.32; N: 6.53.

EXAMPLE 31

2-(N-Benzyl-N-methylamino)-1-phenylethyl 5-diisobutoxyphosphinyl-2,6-dimethyl-4-(3-nitrophenyl)-1,4-dihydropyridine-3-carboxylate. Pale yellow oil (as a mixture of diastereomers). Picrate melts at 122°–8° C.

Elementary analysis for: $C_{38}H_{48}N_3O_7P \cdot C_6H_3N_3O_7$, Calculate (%): C: 57.51; H: 5.59; N: 9.15; Determined (%): C: 57.38; H: 5.63; N: 9.22.

EXAMPLE 32

Methyl 5-di-n-butoxyphosphinyl-2,6-dimethyl-4-(3-nitrophenyl)-1,4-dihydropyridine-3-carboxylate. Melting point 152°–4° C.

Elementary analysis for: $C_{23}H_{33}N_2O_7P$, Calculated (%): C: 57.49; H: 6.92; N: 5.83; Determined (%): C: 57.51; H: 6.99; N: 5.85.

EXAMPLE 33

Ethyl 5-di-n-butoxyphosphinyl-2,6-dimethyl-4-(3-nitrophenyl)-1,4-dihydropyridine-3-carboxylate. Melting point 107°–9° C.

Elementary analysis for: $C_{24}H_{35}N_2O_7P$, Calculated (%): C: 58.29; H: 7.13; N: 5.66; Determined (%): C: 58.31; H: 7.24; N: 5.66.

EXAMPLE 34

Ethyl 5-di-n-butoxyphosphinyl-2,6-dimethyl-4-(3-nitrophenyl)-1,4-dihydropyridine-3-carboxylate. Pale yellow oil. Picrate melts at 101°–3° C.

Elementary analysis for: $C_{32}H_{44}N_3O_7P \cdot C_6H_3N_3O_7$, Calculated (%): C: 54.15; H: 5.62; N: 9.97; Determined (%): C: 54.20; H: 5.68; N: 10.09.

EXAMPLE 35

2-n-Propoxyethyl 5-di-n-butoxyphosphinyl-2,6-dimethyl-4-(3-nitrophenyl)-1,4-dihydropyridine-3-carboxylate. Melting point 94°–6° C.

Elementary analysis for: $C_{27}H_{41}N_2O_8P$ Calculated (%): C: 58.68; H: 7.48; N: 5.07; Determined (%): C: 58.31; H: 7.69; N: 5.10.

EXAMPLE 36

2-Dimethylaminoethyl 5-di-n-butoxyphosphinyl-2,6-dimethyl-4-(3-nitrophenyl)-1,4-dihydropyridine-3-carboxylate. Melting point 101°–3° C.

Elementary analysis for: $C_{26}H_{40}N_3O_7P$, Calculated (%): C: 58.09; H: 7.50; N: 7.82; Determined (%): C: 57.76; H: 7.85; N: 7.85.

EXAMPLE 37

Methyl 5-di-sec-butoxyphosphinyl-2,6-dimethyl-4-(3-nitrophenyl)-1,4-dihydropyridine-3-carboxylate. Melting point 164°–6° C.

Elementary analysis for: $C_{23}H_{33}N_2O_7P$, Calculated (%): C: 57.49; H: 6.92; N: 5.83; Determined (%): C: 57.25; H: 7.13; N: 5.74.

EXAMPLE 38

Ethyl 5-di-sec-butoxyphosphinyl-2,6-dimethyl-4-(3-nitrophenyl)-1,4-dihydropyridine-3-carboxylate. Melting point 150°–2° C.

Elementary analysis for: $C_{24}H_{35}N_2O_7P$, Calculated (%): C: 58.29; H: 7.13; N: 5.66; Determined (%): C: 58.13; H: 7.18; N: 5.68.

EXAMPLE 39

2-(N-Benzyl-N-methylamino)-ethyl 5-di-sec-butoxyphosphinyl-2,6-dimethyl-4-(3-nitrophenyl)-1,4-dihydropyridine-3-carboxylate. Melting point 114°–16° C.

Elementary analysis for: $C_{32}H_{44}N_3O_7P$, Calculated (%): C: 62.63; H: 7.23; N: 6.85; Determined (%): C: 62.37; H: 7.46; N: 6.77.

EXAMPLE 40

2-n-Propoxyethyl 5-di-sec-butoxyphosphinyl-2,6-dimethyl-4-(3-nitrophenyl)-1,4-dihydropyridine-3-carboxylate. Melting point 104°–6° C.

Elementary analysis for: $C_{27}H_{41}N_2O_8P$, Calculated (%): C: 58.68; H: 7.48; N: 5.07; Determined (%): C: 58.53; H: 7.75; N: 5.06.

EXAMPLE 41

Methyl 2,6-dimethyl-4-(3-nitrophenyl)-5-diisopentyloxyphosphinyl-1,4-dihydropyridine-3-carboxylate. Melting point 160°–1° C.

Elementary analysis for: $C_{25}H_{37}N_2O_7P$, Calculated (%): C: 59.04; H: 7.33; N: 5.51; Determined (%): C: 58.98; H: 7.52; N: 5.54.

EXAMPLE 42

2-(N-Benzyl-N-methylamino)-ethyl 2,6-dimethyl-4-(3-nitrophenyl)-5-diisopentyloxyphosphinyl-1,4-dihydropyridine-3-carboxylate. Pale yellow oil. Picrate melts at 117.5°–8° C.

Elementary analysis for: $C_{34}H_{48}N_3O_7P \cdot C_6H_3N_3O_7$, Calculated (%): C: 55.17; H: 5.90; N: 9.65; Determined (%): C: 54.93; H: 5.82; N: 9.53.

EXAMPLE 43

Methyl 5-dicyclopentyloxyphosphinyl-2,6-dimethyl-4-(3-nitrophenyl)-1,4-dihydropyridine-3-carboxylate. Melting point 202°–4° C.

Elementary analysis for: $C_{25}H_{33}N_2O_7P$, Calculated (%): C: 59.52; H: 6.59; N: 5.55; Determined (%): C: 59.24; H: 6.58; N: 5.58.

EXAMPLE 44

Ethyl 5-dicyclopentyloxyphosphinyl 2,6-dimethyl-4-(3-nitrophenyl)-1,4-dihydropyridine-3-carboxylate. Pale yellow oil. Picrate melts at 103°–5° C.

Elementary analysis for: $C_{34}H_{44}N_3O_7P \cdot C_6H_3N_3O_7$, Calculated (%): C: 55.43; H: 5.47; N: 9.70; Determined (%): C: 55.30; H: 5.32; N: 9.52.

EXAMPLE 45

Methyl 2,6-dimethyl-4-(3-nitrophenyl)-5-dineopentyloxyphosphinyl-1,4-dihydropyridine-3-carboxylate. Melting point 241°–2° C.

Elementary analysis for: $C_{25}H_{37}N_2O_7P$, Calculated (%): C: 59.04; H: 7.33; N: 5.51; Determined (%): C: 58.82; H: 7.60; N: 5.33.

EXAMPLE 46

2-(N-Benzyl-N-methylamino)-ethyl 2,6-dimethyl-4-(3-nitrophenyl)-5-dineopentyloxyphosphinyl-1,4-dihydropyridine-3-carboxylate. Pale yellow oil.

IR (film, cm$^{-1}$): 3290, 3230, 3100, 1700, 1655, 1535, 1350, 1240, 1220, 980.

EXAMPLE 47

Methyl 5-diallyloxyphosphinyl-2,6-dimethyl-4-(3-nitrophenyl)-1,4-dihydropyridine-3-carboxylate. Melting point 164°–6° C.

Elementary analysis for: $C_{21}H_{25}N_2O_7P$, Calculated (%): C: 56.25; H: 5.62; N: 6.25; Determined (%): C: 56.12; H: 5.67; N: 6.09.

EXAMPLE 48

2-(N-Benzyl-N-methylamino)-ethyl 5-diallyloxyphosphinyl-2,6-dimethyl-4-(3-nitrophenyl)-1,4-dihydropyridine-3-carboxylate. Pale yellow oil. Picrate melts at 136°–8° C.

Elementary analysis for: $C_{30}H_{36}N_3O_7P \cdot C_6H_3N_3O_7 \cdot \frac{1}{2}H_2O$, Calculated (%): C: 53.34; H: 4.85; N: 10.37; Determined (%): C: 53.42; H: 4.86; N: 10.13.

EXAMPLE 49

Methyl 5-di-(2-methoxyethoxy)-phosphinyl-2,6-dimethyl-4-(3-nitrophenyl)-1,4-dihydropyridine-3-carboxylate. Melting point 144°–6° C.

Elementary analysis for: $C_{21}H_{29}N_2O_9P$, Calculated (%): C: 52.07; H: 6.03; N: 5.78; Determined (%): C: 51.73; H: 6.26; N: 5.79.

EXAMPLE 50

2-(N-Benzyl-N-methylamino)-ethyl 5-di-(2-methoxyethoxy)-phosphinyl-2,6-dimethyl-4-(3-nitrophenyl)-1,4-dihydropyridine-3-carboxylate. Pale yellow oil.

IR (film, cm$^{-1}$): 3240, 3200, 3085, 1700, 1530, 1350, 1240, 1220, 1095, 1035, 965, 845.

EXAMPLE 51

Methyl 2,6-dimethyl-4-(3-nitrophenyl)-5-diphenoxyphosphinyl-1,4-dihydropyridine-3-carboxylate. Melting point 193°–5° C.

Elementary analysis for: $C_{27}H_{25}N_2O_7P$, Calculated (%): C: 62.31; H: 4.84; N: 5.38; Determined (%): C: 62.19; H: 4.78; N: 5.30.

EXAMPLE 52

2-(N-Benzyl-N-methylamino)-ethyl 2,6-dimethyl-4-(3-nitrophenyl)-5-diphenoxyphosphinyl-1,4-dihydropyridine-3-carboxylate. Melting point 130°–5° C.

Elementary analysis for: $C_{36}H_{36}N_3O_7P$, Calculated (%): C: 66.15; H: 5.55; N: 6.43; Determined (%): C: 66.18; H: 5.45; N: 6.36.

EXAMPLE 53

Methyl 4-(2-chlorophenyl)-2,6-dimethyl-5-diisopropoxyphosphinyl-1,4-dihydropyridine-3-carboxylate. Melting point 174°–5° C.

Elementary analysis for: $C_{21}H_{29}ClNO_5P$, Calculated (%): C: 57.07; H: 6.61; N: 3.16; Determined (%): C: 57.06; H: 6.85; N: 3.31.

EXAMPLE 54

2-(N-Benzyl-N-methylamino)-ethyl 4-(2-chlorophenyl)-2,6-dimethyl-5-diisopropoxyphosphinyl-1,4-dihydropyridine-3-carboxylate. Pale yellow oil.

IR (film, cm$^{-1}$): 3300, 3250, 1700, 1650, 1605, 1505, 1220, 990.

EXAMPLE 55

Methyl 4-(3-chlorophenyl)-2,6-dimethyl-5-diisopropoxyphosphinyl-1,4-dihydropyridine-3-carboxylate. Melting point 176°–8° C.

Elementary analysis for: $C_{21}H_{29}ClNO_5P$, Calculated (%): C: 57.07; H: 6.61; N: 3.16; Determined (%): C: 57.19; H: 6.69; N: 3.10.

EXAMPLE 56

2-(N-Benzyl-N-methylamino)-ethyl 4-(3-chlorophenyl)-2,6-dimethyl-5-diisopropoxyphosphinyl-1,4-dihydropyridine-3-carboxylate. Pale yellow oil. Picrate melts at 130°–4° C.

Elementary analysis for: $C_{30}H_{40}ClN_2O_5P \cdot C_6H_3N_3O_7$, Calculated (%): C: 53.76; H: 5.38; N: 8.70; Determined (%): C: 53.56; H: 5.41; N: 8.61.

EXAMPLE 57

Methyl 4-(2-cyanophenyl)-2,6-dimethyl-5-diisopropoxyphosphinyl-1,4-dihydropyridine-3-carboxylate. Melting point 162°–4° C.

Elementary analysis for: $C_{22}H_{29}N_2O_5P$, Calculated (%): C: 61.10; H: 6.75; N: 6.47; Determined (%): C: 61.07; H: 6.82; N: 6.36.

EXAMPLE 58

2-(N-Benzyl-N-methylamino)-ethyl 4-(2-cyanophenyl)-2,6-dimethyl-5-diisopropoxyphosphinyl-1,4-dihydropyridne-3-carboxylate. Pale yellow oil.

IR (film, cm$^{-1}$): 3300, 3240, 2250, 1700, 1650, 1510, 1240, 990.

EXAMPLE 59

Methyl 2,6-dimethyl-5-diisopropoxyphosphinyl-4-(2-trifluoromethylphenyl)-1,4-dihydropyridine-3-carboxylate. Melting point 142°–5° C.

Elementary analysis for: $C_{22}H_{29}F_3NO_5P \cdot \frac{1}{2}H_2O$, Calculated (%): C: 54.54; H: 6.24; N: 2.89; Determined (%): C: 54.69; H: 6.59; N: 2.96.

EXAMPLE 60

2-(N-Benzyl-N-methylamino)-ethyl 2,6-dimethyl-5-diisopropoxyphosphinyl-4-(2-trifluoromethylphenyl)-1,4-dihydropyridine-3-carboxylate. Pale yellow oil.

IR (film, cm$^{-1}$): 3290, 3240, 1700, 1645, 1500, 1230, 990.

EXAMPLE 61

Methyl 2,6-dimethyl-5-diisopropoxyphosphinyl-4-(3-trifluoromethylphenyl)-1,4-dihydropyridine-3-carboxylate. Melting point 191°–2.5° C.

Elementary analysis for: $C_{22}H_{29}F_3NO_5P$, Calculated (%): C: 55.57; H: 6.14; N: 2.94; Determined (%): C: 55.65; H: 6.20; N: 2.78.

EXAMPLE 62

2-(N-Benzyl-N-methylamino)-ethyl 2,6-dimethyl-5-diisopropoxyphosphinyl-4-(3-trifluoromethylphenyl)-1,4-dihydropyridine-3-carboxylate. Pale yellow oil. Picrate melts at 114°–7° C.

Elementary analysis for: $C_{31}H_{40}F_3N_2O_5P \cdot C_6H_3N_3O_7 \cdot \frac{1}{2}H_2O$, Calculated (%): C: 52.48; H: 5.24; N: 8.27; Determined (%): C: 52.46; H: 5.39; N: 8.25.

EXAMPLE 63

Ethyl 5-diethoxyphosphinyl-2,6-dimethyl-4-(2-nitrophenyl)-1,4-dihydropyridine-3-carboxylae. Melting point 127°–30° C.

Elementary analysis for: $C_{20}H_{27}N_2O_7P$, Calculated (%): C: 54.79; H: 6.21; N: 6.39; Determined (%): C: 54.76; H: 6.28; N: 6.22.

EXAMPLE 64

Methyl 2,6-dimethyl-5-di-(1-methylbutoxy)-phosphinyl-4-(3-nitrophenyl)-1,4-dihydropyridine-3-carboxylate. Melting point 160°–1° C.

Elementary analysis for: $C_{25}H_{37}N_2O_7P$, Calculated (%): C: 59.04; H: 7.33; N: 5.51; Determined (%): C: 58.87; H: 7.48; N: 5.31.

EXAMPLE 65

2-(N-Benzyl-N-methylamino)-ethyl 2,6-dimethyl-5-di-(1-methylbutoxy)-phosphinyl-4-(3-nitrophenyl)-1,4-dihydropyridine-3-carboxylate. Pale yellow oil.

IR (film, cm$^{-1}$): 3290, 3225, 3100, 1700, 1650, 1530, 1500, 1350, 1240, 1220, 975.

EXAMPLE 66

Methyl 5-di-(2-ethoxyethoxy)-phosphinyl-2,6-dimethyl-4-(3-nitrophenyl)-1,4-dihydropyridine-3-carboxylate. Melting point 129°–31° C.

Elementary analysis for: $C_{23}H_{33}N_2O_9P$, Calculated (%): C: 53.90; H: 6.49; N: 5.47; Determined (%): C: 53.66; H: 6.72; N: 5.59.

EXAMPLE 67

2-(N-Benzyl-N-methylamino)-ethyl 5-di-(2-ethoxyethoxy)-phosphinyl-2,6-dimethyl-4-(3-nitrophenyl)-1,4-dihydropyridine-3-carboxylate.

Melting point 51°–2° C.

Elementary analysis for: $C_{32}H_{44}N_3O_9P$, Calculated (%): C: 59.53; H: 6.87; N: 6.51; Determined (%): C: 59.84; H: 6.98; N: 6.52.

EXAMPLE 68

Methyl 5-diallyloxyphosphinyl-2,6-dimethyl-4-(3-nitrophenyl)-1,4-dihydropyridine-3-carboxylate. Melting point 94°–6° C.

Elementary analysis for: $C_{24}H_{32}N_3O_7P$, Calculated (%): C: 57.02; H: 6.38; N: 8.31; Determined (%): C: 56.80; H: 6.38; N: 8.35.

EXAMPLE 69

2-n-Propoxyethyl 5-diallyloxyphosphinyl-2,6-dimethyl-4-(3-nitrophenyl)-1,4-dihydropyridine-3-carboxylate. Melting point 91°–3° C.

Elementary analysis for: $C_{25}H_{33}N_2O_8P$, Calculated (%): C: 57.69; H: 6.39; N: 5.38; Determined (%): C: 57.54; H: 6.52; N: 5.47.

EXAMPLE 70

Methyl 4-(2,3-dichlorophenyl)-2,6-dimethyl-5-diisopropoxyphosphinyl-1,4-dihydropyridine-3-carboxylate. Melting point 181°–4° C.

Elementary analysis for: $C_{21}H_{28}Cl_2NO_5P$, Calculated (%): C: 52.95; H: 5.93; N: 2.94; Determined (%): C: 53.12; H: 6.09; N: 3.04.

EXAMPLE 71

2-(N-Benzyl-N-methylamino)-ethyl 4-(2,3-dichlorophenyl)-2,6-dimethyl-5-diisopropoxyphosphinyl-1,4-dihydropyridine-3-carboxylate.

Melting point 109°–11° C.

Elementary analysis for: $C_{30}H_{39}Cl_2N_2O_5P$, Calculated (%): C: 59.12; H: 6.49; N: 4.60; Determined (%): C: 59.15; H: 6.55; N: 4.79.

EXAMPLE 72

Methyl 2,6-dimethyl-4-(3-nitrophenyl)-5-di(tetrahydrofurfuryloxy)phosphinyl-1,4-dihydropyridine-3-carboxylate. Melting point 170°–1° C.

Elementary analysis for: $C_{25}H_{33}N_2O_9P$, Calculated (%): C: 55.97; H: 6.20; N: 5.22; Determined (%): C: 55.76; H: 6.22; N: 5.33.

EXAMPLE 73

2-(N-Benzyl-N-methylamino)-ethyl 2,6-dimethyl-4-(3-nitrophenyl)-5-di-(tetrahydrofurfuryloxy)-phosphinyl-1,4-dihydropyridine-3-carboxylate. Pale yellow oil.

IR (film, cm$^{-1}$): 3290, 3230, 3100, 1700, 1680, 1650, 1530, 1500, 1350, 1240, 1210, 1030.

Similarly prepared were the compounds shown in the following table under Examples 74 to 180, inclusive. All of these compounds were identified by their elementary analysis. Where the products were oils, they were identified by measuring their infrared absorption spectra. The compounds of Examples 74–180 are of formula (I), wherein $R^3$ and $R^5$ are each methyl, and $R^1$, $R^2$, $R^4$, $R^6$ and $R^7$ are as set forth in the table below. In each of these compounds, $R^1$ and $R^2$ are the same and are as set forth in Table 3. With reference to $R^6$ and $R^7$, $R^6$ is hydrogen and $R^7$ is as specified in the table for all but those Examples where the designation "2,3-Cl$_2$" appears, such as Example 83. The designation "2,3-Cl$_2$" means that $R^6$ is 2-chloro and $R^7$ is 3-chloro.

TABLE 3

| Example Numbers | OR$^1$, OR$^2$ | R$^4$ | R$^6$, R$^7$ | Melting Point (°C.) | Recrystallization Solvent |
|---|---|---|---|---|---|
| 74 | iso-propoxy | tetrahydrofurfuryl | 3-NO$_2$ | 170–1 | AcOEt—Et$_2$O |
| 75 | 2-methylallyloxy | Me | 3-NO$_2$ | 179–80 | AcOEt—Et$_2$O |
| 76 | 2-methoxyethoxy | 2-dimethylaminoethyl | 3-NO$_2$ | 77–9 | Et$_2$O |
| 77 | 2-methoxyethoxy | propoxyethyl | 3-NO$_2$ | 74–6 | Et$_2$O |
| 78 | crotyloxy | Me | 3-NO$_2$ | 136–8 | AcOEt—Et$_2$O |
| 79 | crotyloxy | 2-(N—benzyl-N—methylamino)-ethyl | 3-NO$_2$ | (picrate 102–4) | |
| 80 | 2-isopropoxyethoxy | Me | 3-NO$_2$ | 133–4 | AcOEt—Et$_2$O |
| 81 | 2-isopropoxyethoxy | 2-(N—benzyl-N—methylamino)-ethyl | 3-NO$_2$ | 76–8 | Et$_2$O |
| 82 | 2-methylallyloxy | 2-(N—benzyl-N— | 3-NO$_2$ | (oil) | |

TABLE 3-continued

| Example Numbers | $OR^1$, $OR^2$ | $R^4$ | $R^6$, $R^7$ | Melting Point (°C.) | Recrystallization Solvent |
|---|---|---|---|---|---|
| | | methylamino)-ethyl | | | |
| 83 | allyloxy | Me | 2,3-$Cl_2$ | 181–2 | AcOEt—$Et_2O$ |
| 84 | isopropoxy | 2-methylthioethyl | 3-$NO_2$ | 150.5–1 | AcOEt—$Et_2O$ |
| 85 | 3-butenyl-2-oxy | Me | 3-$NO_2$ | 163–5 | AcOEt |
| 86 | 3-butenyl-2-oxy | 2-(N—benzyl-N—methylamino)-ethyl | 3-$NO_2$ | 93–5 | $Et_2O$ |
| 87 | allyloxy | Me | 3-$CF_3$ | 122–4 | AcOEt—$Et_2O$ |
| 88 | 3-methoxy-3-methyl-butoxy | Me | 3-$NO_2$ | 130–1 | $Et_2O$ |
| 89 | 3-methoxy-3-methyl-butoxy | 2-(N—benzyl-N—methyl-amino)-ethyl | 3-$NO_2$ | 83–5 | $Et_2O$ |
| 90 | allyloxy | Me | 2-$CF_3$ | 105–7 | $Et_2O$-hexane |
| 91 | allyloxy | 2-(N—benzyl-N—methylamino)-ethyl | 2-$CF_3$ | (oil) | |
| 92 | 1-ethylpropoxy | Me | 3-$NO_2$ | 179–80 | AcOEt |
| 93 | 1-ethylpropoxy | 2-(N—benzyl-N—methylamino)-ethyl | 3-$NO_2$ | 126–7 | $Et_2O$ |
| 94 | allyloxy | 2-(N—benzyl-N—methylamino)-ethyl | 3-$CF_3$ | (oil) | |
| 95 | 3-methyl-2-butoxy | Me | 3-$NO_2$ | 195–7 | AcOEt—$Et_2O$ |
| 96 | 3-methyl-2-butoxy | 2-(N—benzyl-N—methylamino)-ethyl | 3-$NO_2$ | 136–8 | n-hexane-$Et_2O$ |
| 97 | pentyloxy | 2-(N—benzyl-N—methylamino)-ethyl | 3-$NO_2$ | (picrate 116–8) | |
| 98 | pentyloxy | Me | 3-$NO_2$ | 134–6 | AcOEt—$Et_2O$ |
| 99 | allyloxy | 2-(N—benzyl-N—methylamino)-ethyl | 2,3-$Cl_2$ | (oil) | |
| 100 | isopropoxy | 3-pyridylmethyl | 3-$NO_2$ | 175–6 | AcOEt—$Et_2O$ |
| 101 | isopropoxy | 3-methoxy-3-methylbutyl | 3-$NO_2$ | 130–1 | $Et_2O$ |
| 102 | isopropoxy | 2-methoxy-1-methoxymethyl-ethyl | 3-$NO_2$ | 125–5.5 | $Et_2O$ |
| 103 | isopropoxy | 2-(4-benzyl-1-piperazinyl)-ethyl | 3-$NO_2$ | 154–5 | $Et_2O$ |
| 104 | 2-methoxyethoxy | Me | 3-$CF_3$ | 111–3 | AcOEt |
| 105 | 2-methoxyethoxy | Me | 2-$CF_3$ | 105–7 | AcOEt—$Et_2O$ |
| 106 | 2-methoxyethoxy | Me | 2,3-$Cl_2$ | 133–5 | AcOEt—$Et_2O$ |
| 107 | 2-methoxyethoxy | 2-(N—benzyl-N—methylamino)-ethyl | 3-$CF_3$ | (oil) | |
| 108 | 2-methylallyloxy | Me | 3-$CF_3$ | 145–7 | AcOEt—$Et_2O$ |
| 109 | 2-hexyloxy | Me | 3-$NO_2$ | 137–9 | AcOEt—$Et_2O$ |
| 110 | 2-hexyloxy | 2-(N—benzyl-N—methylamino)-ethyl | 3-$NO_2$ | 61–3 | n-hexane-$Et_2O$ |
| 111 | 3-hexyloxy | Me | 3-$NO_2$ | 153–5 | AcOEt—$Et_2O$ |
| 112 | 3-hexyloxy | 2-(N—benzyl-N—methylamino)-ethyl | 3-$NO_2$ | 97–9 | n-hexane-$Et_2O$ |
| 113 | 2-pentyloxy | Me | 2,3-$Cl_2$ | 152–4 | n-hexane-$Et_2O$ |
| 114 | 2-pentyloxy | Me | 3-$CF_3$ | 116–7 | n-hexane-$Et_2O$ |
| 115 | isopropoxy | benzyl | 3-$NO_2$ | 150–1 | AcOEt—$Et_2O$ |
| 116 | hexyloxy | Me | 3-$NO_2$ | 121–3 | n-hexane-$Et_2O$ |
| 117 | hexyloxy | 2-(N—benzyl-N—methylamino)-ethyl | 3-$NO_2$ | (picrate 117–9) | |
| 118 | heptyloxy | Me | 3-$NO_2$ | 124–6 | AcOEt—hexane |
| 119 | heptyloxy | 2-(N—benzyl-N—methylamino)-ethyl | 3-$NO_2$ | (picrate 82–4) | |
| 120 | 2-methallyloxy | 2-(N—benzyl-N—methylamino)-ethyl | 3-$CF_3$ | (oil) | |
| 121 | 2-methallyloxy | 2-(N—benzyl-N—methylamino)-ethyl | 2,3-$Cl_2$ | (oil) | |
| 122 | 2-pentyloxy | 2-(N—benzyl-N—methylamino)-ethyl | 3-$CF_3$ | (oil) | |
| 123 | 2-pentyloxy | 2-(N—benzyl-N—methylamino)-ethyl | 2,3-$Cl_2$ | (oil) | |
| 124 | 2-methoxyethoxy | 2-(N—benzyl-N—methylamino)- | 2-$CF_3$ | (oil) | |

TABLE 3-continued

| Example Numbers | $OR^1$, $OR^2$ | $R^4$ | $R^6$, $R^7$ | Melting Point (°C.) | Recrystallization Solvent |
|---|---|---|---|---|---|
| 125 | 2-methoxyethoxy | 2-(N—benzyl-N—methylamino)-ethyl | 2,3-$Cl_2$ | (oil) | |
| 126 | isopropoxy | 2-(N—benzyl-N—methylamino)-1-(N—benzyl-N—methylaminomethyl)-ethyl | 3-$NO_2$ | (oil) | |
| 127 | 1,3-dimethylbutoxy | Me | 3-$NO_2$ | 149-9.5 | n-hexane-AcOEt |
| 128 | 3,3 dimethyl-2-butoxy | Me | 3-$NO_2$ | 221-3 | n-hexane-AcOEt |
| 129 | 3,3-dimethyl-2-butoxy | 2-(N—benzyl-N—methylamino)-ethyl | 3-$NO_2$ | 165-7 | n-hexane-AcOEt |
| 130 | 3-methyl-3-butenyloxy | Me | 3-$NO_2$ | 147-9 | n-hexane-AcOEt |
| 131 | 3-methyl-3-butenyloxy | 2-(N—benzyl-N—methylamino)-ethyl | 3-$NO_2$ | (picrate 110-2) | |
| 132 | tetrahydrofurfuryloxy | 2-methoxy-1-methoxymethyl-ethyl | 3-$NO_2$ | (oil) | |
| 133 | tetrahydrofurfuryloxy | 3-pyridinyl-methyl | 3-$NO_2$ | 124-6 | AcOEt—$Et_2O$ |
| 134 | 2-isopropoxyethoxy | 2-(N—benzyl-N—methylamino)-ethyl | 2,3-$Cl_2$ | (oil) | |
| 135 | 2-isopropoxyethoxy | 2-(N—benzyl-N—methylamino)-ethyl | 3-$CF_3$ | (oil) | |
| 136 | 2-methallyloxy | Me | 2-$CF_3$ | 141-2 | AcOEt—$Et_2O$ |
| 137 | 1,3-dimethylbutoxy | 2-(N—benzyl-N—methylamino)-ethyl | 3-$NO_2$ | (oil) | |
| 138 | 1,3-dimethylbutoxy | 2-(N—benzyl-N—methylamino)-ethyl | 3-$NO_2$ | (oil) | |
| 139 | 1-ethylallyloxy | Me | 3-$NO_2$ | 179-80 | AcOEt—$Et_2O$ |
| 140 | 1-ethylallyloxy | 2-(N—benzyl-N—methylamino)-ethyl | 3-$NO_2$ | 113-4 | n-hexane-AcOEt |
| 141 | 2-methallyloxy | 2-(N—benzyl-N—methylamino)-ethyl | 2-$CF_3$ | (oil) | |
| 142 | 3-methoxy-3-methylbutoxy | 2-(N—benzyl-N—methylamino)-ethyl | 3-$CF_3$ | (oil) | |
| 143 | 3-methoxy-3-methylbutoxy | 2-(N—benzyl-N—methylamino)-ethyl | 2-$CF_3$ | (oil) | |
| 144 | 2-isopropoxyethoxy | 2-(N—benzyl-N—methylamino)-ethyl | 2-$CF_3$ | (oil) | |
| 145 | cyclopropylmethoxy | 2-(N—benzyl-N—methylamino)-ethyl | 3-$NO_2$ | (picrate 101-3) | |
| 146 | benzyloxy | 2-(N—benzyl-N—methylamino)-ethyl | 3-$NO_2$ | (picrate 119-21) | |
| 147 | cyclopropylmethoxy | Me | 3-$NO_2$ | 186-8 | AcOEt—$Et_2O$ |
| 148 | benzyloxy | Me | 3-$NO_2$ | 172-4 | AcOEt—$Et_2O$ |
| 149 | isopropoxy | 2-pyridinyl-methyl | 3-$NO_2$ | 148-9 | AcOEt—$Et_2O$ |
| 150 | 3-butenyloxy | Me | 3-$NO_2$ | 148-50 | AcOEt—$Et_2O$ |
| 151 | 3-butenyloxy | 2-(N—benzyl-N—methyl-amino)-ethyl | 3-$NO_2$ | (picrate 102-4) | |
| 152 | 2-isopropoxy-ethoxy | Me | 3-$CF_3$ | 89-91 | h-hexane-$Et_2O$ |
| 153 | 2-isopropoxy-ethoxy | Me | 2-$CF_3$ | (oil) | |
| 154 | 2-isopropoxy-ethoxy | Me | 2,3-$Cl_2$ | 113-5 | iso-$Pr_2O$ |
| 155 | 3-methoxy-3-methylbutoxy | Me | 3-$CF_3$ | 128-9 | n-hexane-$Et_2O$ |
| 156 | 3-methoxy-3-methylbutoxy | Me | 2-$CF_3$ | 65-8 | n-hexane-$Et_2O$ |
| 157 | tetrahydrofurfuryloxy | 2-(N—benzyl-N—methyl-amino)-ethyl | 3-$CF_3$ | (oil) | |
| 158 | tetrahydrofurfuryloxy | Me | 3-$CF_3$ | 123-4 | iso-$Pr_2O$ |
| 159 | 3-methylbutenyl- | 2-(N—benzyl-N—methyl- | 2-$CF_3$ | (oil) | |

TABLE 3-continued

| Example Numbers | OR¹, OR² | R⁴ | R⁶, R⁷ | Melting Point (°C.) | Recrystallization Solvent |
|---|---|---|---|---|---|
| | oxy | amino)-ethyl | | | |
| 160 | 2-methallyloxy | Me | 2,3-Cl₂ | 133–5 | iso-Pr₂O |
| 161 | 2-pentyloxy | Me | 2-CF₃ | 119–20 | n-hexane |
| 162 | allyloxy | 2-(N—benzyl-N—methyl-amino)-ethyl | 2-NO₂ | (oil) | |
| 163 | 3-butynyloxy | Me | 3-NO₂ | 140–4 | n-hexane-AcOEt |
| 164 | allyloxy | Me | 2-NO₂ | 132–3 | n-hexane-AcOEt |
| 165 | 2-propynyloxy | Me | 3-NO₂ | 185–6 | CH₃CN |
| 166 | 2-propynyloxy | 2-(N—benzyl-N—methyl-amino)-ethyl | 3-NO₂ | 102–3 | AcOEt—Et₂O |
| 167 | 2-heptyloxy | Me | 3-NO₂ | 123.5–4.5 | n-hexane-AcOEt |
| 168 | 2-pentyloxy | 2-(N—benzyl-N—methyl-amino)-ethyl | 2-CF₃ | (oil) | |
| 169 | 2-methoxyethoxy | Me | 2-NO₂ | 103–5 | n-hexane-AcOEt |
| 170 | 3-butynyloxy | 2-(N—benzyl-N—methyl-amino)-ethyl | 3-NO₂ | 92–4 | Et₂O |
| 171 | 2-methoxyethoxy | 2-(N—benzyl-N—methyl-amino)-ethyl | 2-NO₂ | (oil) | |
| 172 | isopropoxy | Me | 2-NO₂ | 164–6 | n-hexane-AcOEt |
| 173 | methallyloxy | Me | -NO₂ | 149–52 | |
| 174 | isopropoxy | 2-(N—benzyl-N—methyl-amino)-ethyl | 2-NO₂ | (oil) | |
| 175 | 2-heptyloxy | 2-(N—benzyl-N—methyl-amino)-ethyl | 3-NO₂ | (oil) | |
| 176 | 2-propynyloxy | Me | 2-NO₂ | 144.5–6 | |
| 177 | 2-propynyloxy | 2-(N—benzyl-N—methyl-amino)-ethyl | 2-NO₂ | (oil) | |
| 178 | allyloxy | Me | 2-OCHF₂ | 129–30 | iso-Pr₂O |
| 179 | allyloxy | 2-(N—benzyl-N—methyl-amino)-ethyl | 2-OCHF₂ | (oil) | |
| 180 | allyloxy | cyclopropylmethyl | 3-NO₂ | 135.5 | |

We claim:

1. A 1,4-Dihydropyridine-3-carboxylate of the formula (I)

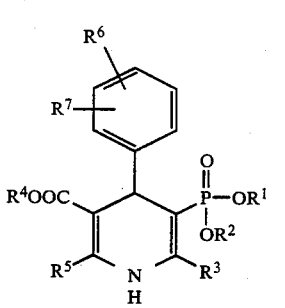

or a pharmaceutically acceptable salt thereof in which:

$R^1$ and $R^2$ are the same or different and are hydrogen; alkyl of 1 to 10 carbon atoms, alkenyl of 2 to 10 carbon atoms, alkynyl of 2 to 10 carbon atoms, cycloalkyl of 3 to 7 carbon atoms, aryl of 6 to 10 carbon atoms, arylalkyl of 7 to 9 carbon atoms, or cycloalkyl-lower alkyl of 3 to 7 carbon atoms in the cycloalkyl moiety, unsubstituted or substituted by halogen or alkoxy of 1 to 4 carbon atoms; or tetrahydrofurfuryl unsubstituted or substituted by alkyl of 1 to 3 carbon atoms;

$R^3$ is lower alkyl, $R^4$ is hydrogen; alkyl of 1 to 10 carbon atoms, alkenyl of 2 to 10 carbon atoms, alkynyl of 2 to 10 carbon atoms, cycloalkyl of 3 to 7 carbon atoms, cycloalkenyl of 3 to 7 carbon atoms, aryl of 6 to 10 carbon atoms, or cycloalkyl-lower alkyl or cycloalkenyl-lower alkyl of 3 to 7 carbon atoms in the cyclic moiety, unsubstituted or substituted by alkoxy of 1 to 3 carbon atoms, aryloxy of 6 to 10 carbon atoms in the aryloxy moiety, aralkyloxy of 6 to 10 carbon atoms in the aralkyloxy moiety, amino, mono- or di-lower alkylamino, alkylthio of 1 to 3 carbon atoms, mono- or di-lower alkylamino-lower alkyl, alkylthioalkyl of 1 to 3 carbon atoms in both alkyl moieties, pyridyl or pyridyl-lower alkyl; tetrahydrofurfuryl unsubstituted or substituted by alkyl of 1 to 3 carbon atoms;

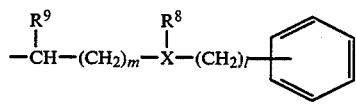

in which X is N or O, $R^8$ is lower alkyl or lower alkenyl when X is N and is not present when X is O, $R^9$ is hydrogen, alkyl of 1 to 3 carbon atoms, phenyl, or

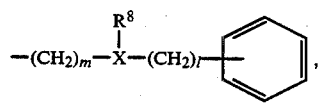

in which $R^8$ and X are as above defined, l is an integer of 0 to 2, and m is an integer of 1 to 4; or

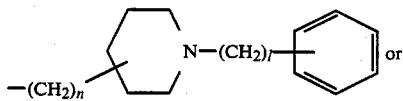

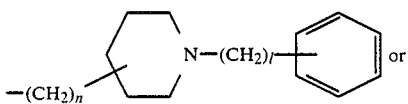

in which l is as defined above and n is an integer of 0 to 2;

$R^5$ is lower alkyl; and $R^6$ and $R^7$ are the same or different and are nitro, cyano, trifluoromethyl, halogen, azide, alkoxycarbonyl of 1 to 3 carbon atoms in the alkoxy moiety, aminocarbonyl, sulfamyl, alkylsulfonyl of 1 to 3 carbon atoms in the alkyl moiety or difluoromethoxy or one of $R^6$ and $R^7$ is hydrogen and the other is as above defined.

2. A compound according to claim 1, wherein $R^1$ and $R^2$ are the same or different and are lower alkyl, lower alkenyl, cycloalkyl of 3 to 7 carbon atoms or cycloalkyl-lower alkyl of 3 to 7 carbon atoms in the cycloalkyl moiety; $R^3$ and $R^5$ are lower alkyl; $R^4$ is

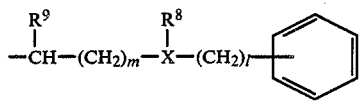

wherein X is N, $R^8$ is lower alkyl, $R^9$ is hydrogen, l is 0 to 2, m is 1-4, $R^6$ is hydrogen and $R^7$ is nitro, trifluoromethyl or difluoromethoxy.

3. A compound according to claim 2, wherein $R^8$ is alkyl of 1 to 3 carbon atoms and l and m are 1.

4. The compound according to claim 1, which is 2-(N-benzyl-N-methylamino)ethyl 2,6-dimethyl-4-(3-nitrophenyl)-5-diisopropoxy-phosphinyl-1,4-dihydropyridine-3-carboxylate.

5. The compound according to claim 1, which is 2-(N-benzyl-N-methylamino)ethyl 5-diallyloxyphosphinyl-2,6-dimethyl-4-(3-nitrophenyl)-1,4-dihydropyridine-3-carboxylate.

6. The compound according to claim 1, wherein $R^1$ and $R^2$ are allyl, $R^3$ and $R^5$ are methyl, $R^4$ is 2-(N-benzyl-N-methylamino)ethyl, $R^6$ is hydrogen and $R^7$ is trifluoromethyl in the 2-position of the depicted phenyl ring.

7. The compound according to claim 1, wherein $R^1$ and $R^2$ are cyclopropylmethyl, $R^3$ and $R^5$ are methyl, $R^4$ is 2-(N-benzyl-N-methylamino)-ethyl, $R^6$ is hydrogen and $R^7$ is nitro in the 3-position of the depicted phenyl ring.

8. The compound according to claim 1, wherein $R^1$ and $R^2$ are 3-butenyl, $R^3$ and $R^5$ are methyl, $R^4$ is 2-(N-benzyl-N-methylamino)d-ethyl, $R^6$ is hydrogen, and $R^7$ is nitro in the 3-position of the depicted phenyl ring.

9. The compound according to claim 1, wherein $R^1$ and $R^2$ are allyl, $R^3$ and $R^5$ are methyl, $R^4$ is 2-(N-benzyl-N-methylamino)ethyl, $R^6$ is hydrogen and $R^7$ is difluoromethoxy in the 2-position of the depicted phenyl ring.

10. A pharmaceutical composition useful for effecting vasodilation and hypotensive activity in humans and animals which comprises a therapeutically effective amount of a compound of the formula (I):

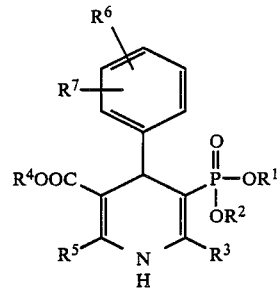

or a pharmaceutically acceptable salt thereof in which:

$R^1$ and $R^2$ are the same or different and are hydrogen; alkyl of 1 to 10 carbon atoms, alkenyl of 2 to 10 carbon atoms, alkynyl of 2 to 10 carbon atoms, cycloalkyl of 3 to 7 carbon atoms, aryl of 6 to 10 carbon atoms, arylalkyl of 7 to 9 carbon atoms, or cycloalkyl-lower alkyl of 3 to 7 carbon atoms in the cycloalkyl moiety, unsubstituted or substituted by halogen or alkoxy of 1 to 4 carbon atoms; or tetrahydrofurfuryl unsubstituted or substituted by alkyl of 1 to 3 carbon atoms;

$R^3$ is lower alkyl, $R^4$ is hydrogen; alkyl of 1 to 10 carbon atoms, alkenyl of 2 to 10 carbon atoms, alkynyl of 2 to 10 carbon atoms, cycloalkyl of 3 to 7 carbon atoms, cycloalkenyl of 3 to 7 carbon atoms, aryl of 6 to 10 carbon atoms, or cycloalkyl-lower alkyl or cycloalkenyl-lower alkyl of 3 to 7 carbon atoms in the cyclic moiety, unsubstituted or substituted by alkoxy of 1 to 3 carbon atoms, aryloxy of 6 to 10 carbon atoms in the aralkyloxy moiety, aralkyloxy of 6 to 10 carbon atoms in the aralkyloxy moiety, amino, mono- or di-lower alkylamino, alkylthio of 1 to 3 carbon atoms, mono- or di-lower alkyl amino-lower alkyl, alkylthioalkyl of 1 to 3 carbon atoms in both alkyl moieties, pyridyl or pyridyl-lower alkyl; tetrahydrofurfuryl unsubstituted or substituted by alkyl of 1 to 3 carbon atoms;

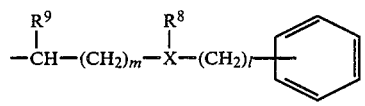

in which X is N or O, $R^8$ is lower alkyl or lower alkenyl when X is N and is not present when X is O, $R^9$ is hydrogen, alkyl of 1 to 3 carbon atoms, phenyl, or

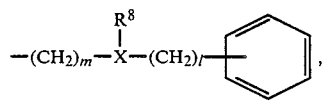

in which $R^8$ and X are as above defined, l is an integer of 0 to 2, and m is an integer of 1 to 4; or

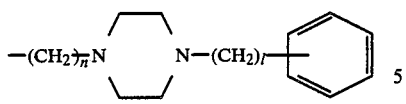

-continued

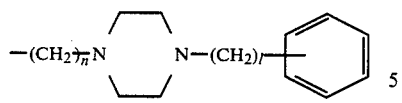

in which l is as defined above and n is an integer of 0 to 2;

$R^5$ is lower alkyl; and $R^6$ and $R^7$ are the same of different and are nitro, cyano, trifluoromethyl, halogen, azide, alkoxycarbonyl of 1 to 3 carbon atoms in the alkoxy moiety, aminocarbonyl, sulfamyl, alkylsulfonyl of 1 to 3 carbon atoms in the alkyl moiety or difluoromethyoxy or one of $R^6$ and $R^7$ is hydrogen and the other is as above defined, in combination with a pharmaceutically acceptable carrier.

11. A composition according to claim 10 wherein $R^1$ and $R^2$ are the same or different and are lower alkyl, lower alkenyl, cycloalkyl of 3 to 7 carbon atoms or cycloalkyl-lower alkyl of 3 to 7 carbon atoms in the cycloalkyl moiety; $R^3$ and $R^5$ are lower alkyl; $R^4$ is

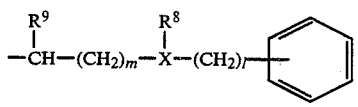

wherein X is N, $R^8$ is lower alkyl, $R^9$ is hydrogen, l is 0 to 2, m is 1-4, $R^6$ is hydrogen and $R^7$ is nitro, trifluoromethyl or difluoromethoxy.

12. A composition according to claim 11 wherein $R^8$ is alkyl of 1 to 3 carbon atoms and l and m are 1.

13. A pharmaceutical composition according to claim 10 wherein the compound is 2-(N-benzyl-N-methylamino)-ethyl 2,6-dimethyl-4-(3-nitrophenyl)-5-diisopropoxy-phosphinyl-1,4-dihydropyridine-3-carboxylate.

14. A pharmaceutical composition according to claim 10 wherein the compound is 2-(N-benzyl-N-methylamino)-ethyl 5-diallyloxyphosphinyl-2,6-dimethyl-4-(3-nitrophenyl)-1,4-dihydropyridine-3-carboxylate.

15. A composition according to claim 10 wherein $R^1$ and $R^2$ are allyl, $R^3$ and $R^5$ are methyl, $R^4$ is 2-(N-benzyl-N-methylamino)-ethyl, $R^6$ is hydrogen and $R^7$ is trifluoromethyl in the 2-position of the depicted phenyl ring.

16. A composition according to claim 10 wherein $R^1$ and $R^2$ are cyclopropylmethyl, $R^3$ and $R^5$ are methyl, $R^4$ is 2-(N-benzyl-N-methylamino)-ethyl, $R^6$ is hydrogen and $R^7$ is nitro in the 3-position of the depicted phenyl ring.

17. A composition according to claim 10 wherein $R^1$ and $R^2$ are 3-butenyl, $R^3$ and $R^5$ are methyl, $R^4$ is 2-(N-benzyl-N-methylamino)-ethyl, $R^6$ is hydrogen, and $R^7$ is nitro in the 3-position of the depicted phenyl ring.

18. A composition according to claim 10 wherein $R^1$ and $R^2$ are allyl, $R^3$ and $R^5$ are methyl, $R^4$ is 2-(N-benzyl-N-methyl-amino)-ethyl, $R^6$ is hydrogen and $R^7$ is difluoromethoxy in the 2-position of the depicted phenyl ring.

19. A method of effecting vasodilation and antihypertensive activity in humans and animals which comprises administering to a human or animal in need thereof a therapeutically effective amount of a compound of the formula (I):

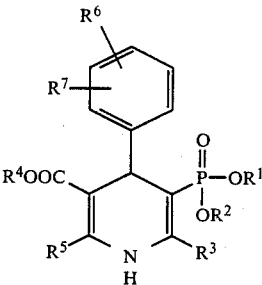

or a pharmaceutically acceptable salt thereof in which:

$R^1$ and $R^2$ are the same or different and are hydrogen; alkyl of 1 to 10 carbon atoms, alkenyl of 2 to 10 carbon atoms, alkynyl of 2 to 10 carbon atoms, cycloalkyl of 3 to 7 carbon atoms, aryl of 6 to 10 carbon atoms, arylalkyl of 7 to 9 carbon atoms, or cycloalkyl-lower alkyl of 3 to 7 carbon atoms in the cycloalkyl moiety, unsubstituted or substituted by halogen or alkoxy or 1 to 4 caron atoms; or tetrahydrofurfuryl unsubstituted or substituted by alkyl of 1 to 3 carbon atoms;

$R^3$ is lower alkyl, $R^4$ is hydrogen; alkyl of 1 to 10 carbon atoms, alkenyl of 2 to 10 carbon atoms, alkynyl of 2 to 10 carbon atoms, cycloalkyl of 3 to 7 carbon atoms, cycloalkenyl of 3 to 7 carbon atoms, aryl of 6 to 10 carbon atoms, or cycloalkyl-lower alkyl or cycloalkenyl-lower alkyl of 3 to 7 carbon atoms in the cyclic moiety, unsubstituted or substituted by alkoxy of 1 to 3 carbon atoms, aryloxy of 6 to 10 carbon atoms in the aryloxy moiety, aralkyloxy of 6 to 10 carbon atoms in the aralkyloxy moiety, amino, mono- or di-lower alkylamino, alkylthio of 1 to 3 carbon atoms, mono- or di-lower alkyloamino-lower alkyl, alkylthioalkyl of 1 to 3 carbon atoms in both alkyl moieties, pyridyl or pyridyl-lower alkyl; tetrahydrofurfuryl unsubstituted or substituted by alkyl of 1 to 3 carbon atoms;

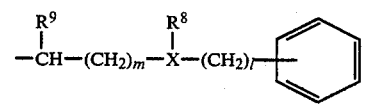

in which X is N or O, $R^8$ is lower alkyl or lower alkenyl when X is N and is not present when X is O, $R^9$ is hydrogen, alkyl of 1 to 3 carbon atoms, phenyl, or

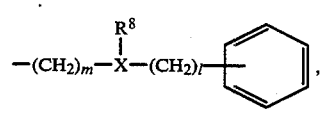

in which $R^8$ and X are as above defined. l is an integer of 0 to 2, and m is an integer of 1 to 4; or

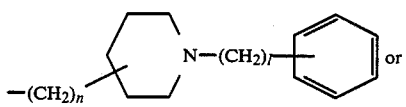

-continued

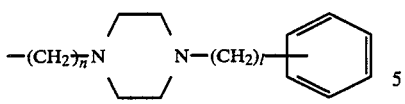

in which l is as defined above and n is integer of 0 to 2;

$R^5$ is lower alkyl; and $R^6$ and $R^7$ are the same or different and are nitro, cyano, trifluoromethyl, halogen, azide, alkoxycarbonyl of 1 to 3 carbon atoms in the alkoxy moiety, aminocarbonyl, sulfamyl, alkylsulfonyl of 1 to 3 carbon atoms in the alkyl moiety or difluoromethoxy or one of $R^6$ and $R^7$ is hydrogen and the other is as above defined, in combination with a pharmaceutically acceptable carrier.

20. A method according to claim 19 wherein $R^1$ and $R^2$ are the same or different and are lower alkyl, lower alkenyl, cycloalkyl of 3 to 7 carbon atoms or cycloalkyl-lower alkyl of 3 to 7 carbon atoms in the cycloalkyl moiety; $R^3$ and $R^5$ are lower alkyl; $R^4$ is

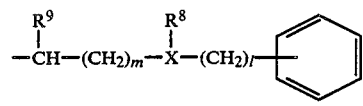

wherein X is N, $R^8$ is lower alkyl, $R^9$ is hydrogen, l is 0 to 2, m is 1–4, $R^6$ is hydrogen and $R^7$ is nitro, trifluoromethyl or difluoromethoxy.

21. A method according to claim 20 wherein $R^8$ is alkyl of 1 to 3 carbon atoms and l and m are 1.

22. A method according to claim 19 wherein the compound is 2-(N-benzyl-N-methylamino)-ethyl 2,6-dimethyl-4-(3-nitrophenyl)-5-diisopropoxy-phosphinyl-1,4-dihydropyridine-3-carboxylate.

23. A method according to claim 19 wherein the compound is 2-(N-benzyl-N-methylamino)-ethyl 5-diallyloxyphosphinyl-2,6-dimethyl-4-(3-nitrophenyl)-1,4-dihydropyridine-3-carboxylate.

24. A method according to claim 19 wherein $R^1$ and $R^2$ are allyl, $R^3$ and $R^5$ are methyl, $R^4$ is 2-(N-benzyl-N-methylamino)-ethyl, $R^6$ is hydrogen and $R^7$ is trifluoromethyl in the 2-position of the depicted phenyl ring.

25. A method according to claim 19 wherein $R^1$ and $R^2$ are cyclopropylmethyl, $R^3$ and $R^5$ are methyl, $R^4$ is 2-(N-benzyl-N-methylamino)-ethyl, $R^6$ is hydrogen and $R^7$ is nitro in the 3-position of the depicted phenyl ring.

26. A method according to claim 19 wherein $R^1$ and $R^2$ are 3-butenyl, $R^3$ and $R^5$ are methyl, $R^4$ is 2-(N-benzyl-N-methylamino)-ethyl, $R^6$ is hydrogen, and $R^7$ is nitro in the 3-position of the depicted phenyl ring.

27. A method according to claim 19 wherein $R^1$ and $R^2$ are allyl, $R^3$ and $R^5$ are methyl, $R^4$ is 2-(N-benzyl-N-methyl-amino)-ethyl, $R^6$ is hydrogen and $R^7$ is difluoromethoxy in the 2-position of the depicted phenyl ring.

28. The compound according to claim 1 which is
2-(N-benzyl-N-methylamino)-ethyl 2,6-dimethyl-4-(3-nitrophenyl)-5-diisopropoxy-phosphinyl-1,4-dihydropyridine-3-carboxylate,
2-(N-Benzyl-N-methylamino)-ethyl 5-diallyloxyphosphinyl-2,6-dimethyl-4-(3-nitrophenyl)-1,4-dihydropyridine-3-carboxylate,
2-(N-Benzyl-N-methylamino)-ethyl 5-di-(2-methoxyethoxy)-phosphinyl-2,6-dimethyl-4-(3-nitrophenyl)-1,4-dihydropyridine-3-carboxylate,
2-(N-Benzyl-N-methylamino)-ethyl 2,6-dimethyl-5-diisopropoxyphosphinyl-4-(2-trifluoromethylphenyl)-1,4-dihydropyridine-3-carboxylate, or
2-(N-Benzyl-N-methylamino)-ethyl 2,6-dimethyl-5-di(1-methylbutoxy)-phosphinyl-4-(3-nitrophenyl)-1,4-dihydropyridine-3-carboxylate.

29. The compound according to claim 1 wherein:
(a) Both $R^1$ and $R^2$ are crotyl; $R^4$ is 2-(N-benzyl-N-methylamino)-ethyl; and one of $R^6$ and $R^7$ is hydrogen and the other is 3-$NO_2$;
(b) Both $R^1$ and $R^2$ are 2-methylallyl; $R^4$ is 2-(N-benzyl-N-methylamino)-ethyl; and one of $R^6$ and $R^7$ is hydrogen and the other is 3-$NO_2$;
(c) Both $R^1$ and $R^2$ are allyl; $R^4$ is methyl; and one of $R^6$ and $R^7$ is hydrogen and the other is 2-$CF_3$;
(d) Both $R^1$ and $R^2$ are allyl; $R^4$ is 2-(N-benzyl-N-methylamino)-ethyl; and one of $R^6$ and $R^7$ is hydrogen and the other is 2-$CF_3$;
(e) Both $R^1$ and $R^2$ are allyl; $R^4$ is 2-(N-benzyl-N-methylamino)-ethyl; and $R^6$ and $R^7$ are 2,3-$Cl_2$;
(f) Both $R^1$ and $R^2$ are 3-methyl-3-butenyl; $R^4$ is 2-(N-benzyl-N-methylamino)-ethyl; and one of $R^6$ and $R^7$ is hydrogen and the other is 3-$NO_2$;
(g) Both $R^1$ and $R^2$ are cyclopropylmethyl; $R^4$ is 2-(N-benzyl-N-methylamino)-ethyl; and one of $R^6$ and $R^7$ is hydrogen and the other is 3-$NO_2$;
(h) Both $R^1$ and $R^2$ are 3-butenyl; $R^4$ is 2-(N-benzyl-N-methylamino)-ethyl; and one of $R^6$ and $R^7$ is hydrogen and the other is 3-$NO_2$;
(i) Both $R^1$ and $R^2$ are 3-methylbutenyl; $R^4$ is 2-(N-benzyl-N-methylamino)-ethyl; and one of $R^6$ and $R^7$ is hydrogen and the other is 2-$CF_3$;
(j) Both $R^1$ and $R^2$ are allyl; $R^4$ is methyl; and one of $R^6$ and $R^7$ is hydrogen and the other is 2-$NO_2$; or
(k) Both $R^1$ and $R^2$ are allyl; $R^4$ is 2-(N-benzyl-N-methylamino)-ethyl; and one of $R^6$ and $R^7$ is hydrogen and the other is 2-$OCHF_2$.

30. A composition according to claim 10 wherein the compound is
2-(N-benzyl-N-methylamino)-ethyl 2,6-dimethyl-4-(3-nitrophenyl)-5-diisopropoxy-phosphinyl-1,4-dihydropyridine-3-carboxylate,
2-(N-Benzyl-N-methylamino)-ethyl 5-diallyloxyphosphinyl-2,6-dimethyl-4-(3-nitrophenyl)-1,4-dihydropyridine-3-carboxylate,
2-(N-Benzyl-N-methylamino)-ethyl 5-di-(2-methoxyethoxy)-phosphinyl-2,6-dimethyl-4-(3-nitrophenyl)-1,4-dihydropyridine-3-carboxylate,
2-(N-Benzyl-N-methylamino)-ethyl 2,6-dimethyl-5-diisopropoxyphosphinyl-4-(2-trifluoromethylphenyl)-1,4-dihydropyridine-3-carboxylate, or
2-(N-Benzyl-N-methylamino)-ethyl 2,6-dimethyl-5-di-(1-methylbutoxy)-phosphinyl-4-(3-nitrophenyl)-1,4-dihydropyridine-3-carboxylate.

31. A composition according to claim 10 wherein:
(a) Both $R^1$ and $R^2$ are crotyl; $R^4$ is 2-(N-benzyl-N-methylamino)-ethyl; and one of $R^6$ and $R^7$ is hydrogen and the other is 3-$NO_2$;
(b) Both $R^1$ and $R^2$ are 2-methylallyl; $R^4$ is 2-(N-benzyl-N-methylamino)-ethyl; and one of $R^6$ and $R^7$ is hydrogen and the other is 3-$NO_2$;
(c) Both $R^1$ and $R^2$ are allyl; $R^4$ is methyl; and one of $R^6$ and $R^7$ is hydrogen and the other is 2-$CF_3$;

(d) Both $R^1$ and $R^2$ are allyl; $R^4$ is 2-(N-benzyl-N-methylamino)-ethyl; and one of $R^6$ and $R^7$ is hydrogen and the other is 2-CF$_3$;

(e) Both $R^1$ and $R^2$ are allyl; $R^4$ is 2-(N-benzyl-N-methylamino)-ethyl; and $R^6$ and $R^7$ are 2,3-Cl$_2$;

(f) Both $R^1$ and $R^2$ are 3-methyl-3-butenyl; $R^4$ is 2-(N-benzyl-N-methylamino)-ethyl; and one of $R^6$ and $R^7$ is hydrogen and the other is 3-NO$_2$;

(g) Both $R^1$ and $R^2$ are cyclopropylmethyl; $R^4$ is 2-(N-benzyl-N-methylamino)-ethyl; and one of $R^6$ and $R^7$ is hydrogen and the other is 3-NO$_3$;

(h) Both $R^1$ and $R^2$ are 3-butenyl; $R^4$ is 2-(N-benzyl-N-methylamino)-ethyl; and one of $R^6$ and $R^7$ is hydrogen and the other is 3-NO$_2$;

(i) Both $R^1$ and $R^2$ are 3-methylbutenyl; $R^4$ is 2-(N-benzyl-N-methylamino)-ethyl; and one of $R^6$ and $R^7$ is hydrogen and the other is 2-CF$_3$;

(j) Both $R^1$ and $R^2$ are allyl; $R^4$ is methyl; and one of $R^6$ and $R^7$ is hydrogen and the other is 2-NO$_2$; or (k) Both $R^1$ and $R^2$ are allyl; $R^4$ is 2-(N-benzyl-N-methylamino)-ethyl; and one of $R^6$ and $R^7$ is hydrogen and the other is 2-OCHF$_2$.

32. A method according to claim 19 wherein the compound is 2-(N-benzyl-N-methylamino)-ethyl 2,6-dimethyl-4-(3-nitrophenyl)-5-diisopropoxy-phosphinyl-1,4-dihydropyridine-3-carboxylate, 2-(N-Benzyl-N-methylamino)-ethyl 5-diallyloxyphosphinyl-2,6-dimethyl-4-(3-nitrophenyl)-1,4-dihydropyridine-3-carboxylate, 2-(N-Benzyl-N-methylamino)-ethyl 5-di-(2-methoxyethoxy)-phosphinyl-2,6-dimethyl-4-(3-nitrophenyl)-1,4-dihydropyridine-3-carboxylate, 2-(N-Benzyl-N-methylamino)-ethyl 2,6-dimethyl-5-diisopropoxyphosphinyl-4-(2-trifluoromethylphenyl)-1,4-dihydropyridine-3-carboxylate, or 2-(N-Benzyl-N-methylamino)-ethyl 2,6-dimethyl-5-di(1-methylbutoxy)-phosphinyl-4-(3-nitrophenyl)-1,4-dihydropyridine-3-carboxylate.

33. A method according to claim 19 wherein:

(a) Both $R^1$ and $R^2$ are crotyl; $R^4$ is 2-(N-benzyl-N-methylamino)-ethyl; and one of $R^6$ and $R^7$ is hydrogen and the other is 3-NO$_3$;

(b) Both $R^1$ and $R^2$ are 2-methylallyl; $R^4$ is 2-(N-benzyl-N-methylamino)-ethyl; and one of $R^6$ and $R^7$ is hydrogen and the other is 3-NO$_2$;

(c) Both $R^1$ and $R^2$ are allyl; $R^4$ is methyl; and one of $R^6$ and $R^7$ is hydrogen and the other is 2-CF$_3$;

(d) Both $R^1$ and $R^2$ are allyl; $R^4$ is 2-(N-benzyl-N-methylamino)-ethyl; and one of $R^6$ and $R^7$ is hydrogen and the other is 2-CF$_3$;

(e) Both $R^1$ and $R^2$ are allyl; $R^4$ is 2-(N-benzyl-N-methylamino)-ethyl; and $R^6$ and $R^7$ are 2,3-Cl$_2$;

(f) Both $R^1$ and $R^2$ are 3-methyl-3-butenyl; $R^4$ is 2-(N-benzyl-N-methylamino)-ethyl; and one of $R^6$ and $R^7$ is hydrogen and the other is 3-NO$_2$;

(g) Both $R^1$ and $R^2$ are cyclopropylmethyl; $R^4$ is 2-(N-benzyl-N-methylamino)-ethyl; and one of $R^6$ and $R^7$ is hydrogen and the other is 3-NO$_2$;

(h) Both $R^1$ and $R^2$ are 3-butenyl; $R^4$ is 2-(N-benzyl-N-methylamino)-ethyl; and one of $R^6$ and $R^7$ is hydrogen and the other is 3-NO$_2$;

(i) Both $R^1$ and $R^2$ are 3-methylbutenyl; $R^4$ is 2-(N-benzyl-N-methylamino)-ethyl; and one of $R^6$ and $R^7$ is hydrogen and the other is 2-CF$_3$;

(j) Both $R^1$ and $R^2$ are allyl; $R^4$ is methyl; and one of $R^6$ and $R^7$ is 2-NO$_2$; or (k) Both $R^1$ and $R^2$ are allyl; $R^4$ is 2-(N-benzyl-N-methylamino)-ethyl; and one of $R^6$ and $R^7$ is hydrogen and the other is 2-OCHF$_2$.

* * * * *